US010383329B2

(12) United States Patent
Abrey et al.

(10) Patent No.: US 10,383,329 B2
(45) Date of Patent: Aug. 20, 2019

(54) PRESERVATIVES

(71) Applicant: Eden Research PLC, York, North Yorkshire (GB)

(72) Inventors: Alexander John Abrey, York (GB); Kenneth William Brooks, York (GB); Arthur Benjamin Norman Gill, York (GB); Clive Roland Newitt, York (GB)

(73) Assignee: Eden Research PLC, Poulton, Cirencester (GB)

( * ) Notice: Subject to any disclaimer, the term of this patent is extended or adjusted under 35 U.S.C. 154(b) by 0 days.

(21) Appl. No.: 14/646,171

(22) PCT Filed: Nov. 21, 2013

(86) PCT No.: PCT/GB2013/053065
§ 371 (c)(1),
(2) Date: May 20, 2015

(87) PCT Pub. No.: WO2014/080199
PCT Pub. Date: May 30, 2014

(65) Prior Publication Data
US 2015/0289503 A1 Oct. 15, 2015

(30) Foreign Application Priority Data
Nov. 21, 2012 (GB) .................................. 1220940.9

(51) Int. Cl.
| *A01N 25/22* | (2006.01) |
| *A61K 47/10* | (2017.01) |
| *A61K 47/08* | (2006.01) |
| *A61K 9/50* | (2006.01) |
| *A01N 25/28* | (2006.01) |
| *A01N 31/08* | (2006.01) |
| *A01N 31/16* | (2006.01) |
| *A01N 35/02* | (2006.01) |
| *A01N 35/06* | (2006.01) |
| *A01N 49/00* | (2006.01) |

(52) U.S. Cl.
CPC ............. *A01N 25/22* (2013.01); *A01N 25/28* (2013.01); *A61K 9/50* (2013.01); *A61K 9/5068* (2013.01); *A61K 47/08* (2013.01); *A61K 47/10* (2013.01); *A61K 9/5089* (2013.01)

(58) Field of Classification Search
None
See application file for complete search history.

(56) References Cited

U.S. PATENT DOCUMENTS

| 3,499,765 A | 3/1970 | Lendvay |
| 3,710,795 A | 1/1973 | Higuchi |
| 3,767,421 A | 10/1973 | Gulstad |
| 3,956,485 A | 5/1976 | Willett |
| 4,001,480 A | 1/1977 | Shank |
| 4,032,551 A | 6/1977 | Willett |
| 4,049,828 A | 9/1977 | Cole |
| 4,310,554 A | 1/1982 | Olson |
| 4,534,983 A | 8/1985 | Koene |
| 4,611,608 A | 9/1986 | Vos |
| 4,617,945 A | 10/1986 | Vos |
| 4,696,863 A | 9/1987 | Matsushita |
| 4,743,620 A | 5/1988 | Hodgin |
| 4,810,646 A | 3/1989 | Jamas ............................ 435/101 |
| 4,826,693 A | 5/1989 | Smith |
| 4,834,977 A | 5/1989 | Takjui |
| 4,889,719 A | 12/1989 | Toshiro |
| 4,944,693 A | 7/1990 | Puerner |
| 4,963,583 A | 10/1990 | Kunz |
| 4,985,261 A | 1/1991 | Kang |
| 4,992,540 A | 2/1991 | Jamas ............................ 536/123 |
| 5,001,155 A | 3/1991 | Kuc |
| 5,013,566 A | 5/1991 | Sampson |
| 5,028,703 A | 7/1991 | Jamas |
| 5,032,401 A | 7/1991 | Spiros |
| 5,068,453 A | 11/1991 | Kuwahara |
| 5,078,904 A | 1/1992 | Behan |
| 5,082,936 A | 1/1992 | Jamas ............................ 536/123 |
| 5,091,200 A | 2/1992 | Kang |
| 5,288,632 A | 2/1994 | Pannell |
| 5,401,727 A | 3/1995 | Rorstad ............................ 514/54 |
| 5,547,677 A | 8/1996 | Wright |
| 5,549,901 A | 8/1996 | Wright |
| 5,576,009 A | 11/1996 | Nastke |
| 5,607,677 A | 3/1997 | Jamas |
| 5,618,840 A | 4/1997 | Wright |
| 5,622,548 A | 4/1997 | Zou |

(Continued)

FOREIGN PATENT DOCUMENTS

| AP | P/2006/003724 | 1/2005 |
| AP | P/2008/004524 | 8/2006 |

(Continued)

OTHER PUBLICATIONS

Dervan, Peter B., "Molecular Recognition of DNA by Small Molecules", Bioorganic & Medicinal Chemistry 9, (2001), 2215-2235.
EPA Regulation 40 C.F.R., Subchapter E—Pesitcide Programs, Part 152—Pesticide Registration and Classification Procedures, 5-44.
U.S. Appl. No. 10/488,130 (2004/0248764), filed Jul. 7, 2004 (Dec. 9, 2004), Lanny Franklin.
U.S. Appl. No. 10/586,597 (2008/0220338), filed Apr. 4, 2008 (Sep. 11, 2008), Lanny Franklin.
U.S. Appl. No. 11/597,116 (2010/0040656), filed Oct. 27, 2008 (Feb. 18, 2010), Lanny Franklin.
U.S. Appl. No. 12/095,580 (2010/0272818), filed Jul. 23, 2009 (Oct. 28, 2010), Lanny Franklin.
U.S. Appl. No. 12/095,584 (2010/0136102), filed Aug. 28, 2009 (Jun. 3, 2010), Lanny Franklin.

(Continued)

Primary Examiner — John Pak
Assistant Examiner — Daniel L Branson
(74) Attorney, Agent, or Firm — Pepper Hamilton LLP

(57) ABSTRACT

There is described a composition comprising a microparticle component; optionally an encapsulated active agent; and a preservative amount of one or more terpenes.

20 Claims, No Drawings

(56) References Cited

U.S. PATENT DOCUMENTS

| | | | |
|---|---|---|---|
| 5,629,021 A | 5/1997 | Wright | |
| 5,662,915 A | 9/1997 | Okioga | |
| 5,662,957 A | 9/1997 | Wright | |
| 5,673,468 A | 10/1997 | Pumpe | |
| 5,700,679 A | 12/1997 | Wright | |
| 5,730,989 A | 3/1998 | Wright | |
| 5,756,136 A | 5/1998 | Black | |
| 5,798,252 A | 8/1998 | Hobson | |
| 5,849,956 A | 12/1998 | Koga | |
| 5,849,959 A | 12/1998 | Pfirmann | |
| 5,919,838 A | 7/1999 | Mizobuchi | |
| 5,922,121 A | 7/1999 | Kwan | |
| 5,939,050 A | 8/1999 | Iyer | |
| 5,965,612 A | 10/1999 | Tse | |
| 5,977,186 A | 11/1999 | Franklin | |
| 5,981,625 A | 11/1999 | Zou | |
| 6,130,253 A | 10/2000 | Franklin | |
| 6,187,439 B1 | 2/2001 | Elwakil | |
| 6,232,528 B1 | 5/2001 | Scorza | |
| 6,242,594 B1 | 6/2001 | Kelly | 536/123.12 |
| 6,246,594 B1 | 6/2001 | Novagen | |
| 6,261,540 B1 | 7/2001 | Nelson | |
| 6,306,450 B1 | 10/2001 | Bank | |
| 6,444,448 B1 | 9/2002 | Wheatcroft | |
| 6,465,640 B1 | 10/2002 | Hood | |
| 6,482,455 B1 | 11/2002 | Freire | |
| 6,506,803 B1 | 1/2003 | Baker, Jr. | |
| 6,506,906 B1 | 1/2003 | Dervan | 548/312.4 |
| 6,524,998 B1 | 2/2003 | Kloepper | |
| 6,534,078 B1 | 3/2003 | Strzemiemski | |
| 6,685,954 B2 | 2/2004 | Jeannin | |
| 6,723,358 B1 | 4/2004 | Van Lengerich | |
| 6,746,684 B2 | 6/2004 | Kitagaki | |
| 6,849,276 B1 | 2/2005 | Dufau | |
| 6,849,476 B2 | 2/2005 | Murakami | |
| 6,887,493 B2 | 5/2005 | Shefer | |
| 7,018,641 B1 | 3/2006 | Momol | |
| 7,226,607 B2 * | 6/2007 | Uchiyama | A61L 9/012 424/401 |
| 9,439,416 B2 | 9/2016 | Franklin | |
| 9,655,360 B2 | 5/2017 | Franklin | |
| 2002/0028256 A1 | 3/2002 | Bessette | |
| 2003/0231978 A1 | 2/2003 | Franklin | |
| 2003/0091657 A1 | 5/2003 | Chiasson | |
| 2003/0130171 A1 | 7/2003 | Schoenhard | |
| 2003/0152629 A1 | 8/2003 | Shefer | |
| 2003/0180349 A1 | 9/2003 | Franklin | |
| 2003/0185956 A1 | 10/2003 | Gradley | |
| 2003/0191046 A1 | 10/2003 | Krzysztof | |
| 2003/0194454 A1 | 10/2003 | Bessette | |
| 2003/0216488 A1 | 11/2003 | Uchiyama | |
| 2003/0228402 A1 | 12/2003 | Franklin | |
| 2003/0231987 A1 | 12/2003 | Carmack | |
| 2004/0022990 A1 | 2/2004 | Sitabkhan | |
| 2004/0054166 A1 | 3/2004 | Sauter | |
| 2004/0096821 A1 | 5/2004 | Keenan | |
| 2004/0248764 A1 | 12/2004 | Franklin | |
| 2005/0118273 A1 | 6/2005 | Sasaki | |
| 2005/0126908 A1 | 6/2005 | Keenan | |
| 2005/0214337 A1 * | 9/2005 | McGee | A01N 25/12 424/405 |
| 2005/0281781 A1 | 12/2005 | Ostroff | |
| 2006/0120974 A1 | 6/2006 | Mcneight | |
| 2006/0127489 A1 | 6/2006 | Crothers | |
| 2006/0165614 A1 | 7/2006 | Nelson | |
| 2008/0220038 A1 | 9/2008 | Franklin | |
| 2010/0040656 A1 | 2/2010 | Franklin | |
| 2010/0247485 A1 | 3/2010 | Kollars | |
| 2010/0136102 A1 * | 6/2010 | Franklin | A01N 25/28 424/451 |
| 2010/0272818 A1 | 10/2010 | Franklin | |
| 2014/0170198 A1 | 6/2014 | Franklin | |
| 2015/0289503 A1 | 10/2015 | Abrey | |
| 2016/0278367 A1 | 9/2016 | Abrey | |
| 2017/0245497 A1 | 8/2017 | Franklin | |

FOREIGN PATENT DOCUMENTS

| | | |
|---|---|---|
| AU | 2002323473 | 8/2002 |
| AU | 2005207622 | 1/2005 |
| AU | 2005245190 | 5/2005 |
| AU | 2006321415 | 8/2006 |
| AU | 2006321416 | 8/2006 |
| CA | 2141761 | 2/1996 |
| CA | 2382740 | 1/2001 |
| CA | 2567333 | 1/2005 |
| CN | 200580024514 | 5/2005 |
| DE | 19720604 | 11/1998 |
| EP | 0085805 | 8/1983 |
| EP | 0242135 | 10/1987 |
| EP | 0252896 | 1/1988 |
| EP | 0414282 | 2/1991 |
| EP | 0414283 | 2/1991 |
| EP | 0460945 | 12/1991 |
| EP | 0528466 | 2/1993 |
| EP | 0819759 | 4/1998 |
| EP | 0844909 | 6/1998 |
| EP | 0913407 | 5/1999 |
| EP | 1085812 | 3/2001 |
| EP | 1106070 | 6/2001 |
| EP | 1161878 | 12/2001 |
| EP | 1161883 | 12/2001 |
| EP | 1240380 | 9/2002 |
| EP | 1413202 | 4/2004 |
| EP | 1420640 | 11/2004 |
| EP | 1753529 | 5/2005 |
| EP | 1159882 | 4/2006 |
| EP | 1711058 | 10/2006 |
| EP | 2168737 | 7/2007 |
| EP | 1954130 | 8/2008 |
| EP | 1538197 | 11/2012 |
| EP | 1954129 | 8/2013 |
| GB | 1285244 | 8/1972 |
| GB | 1362007 | 7/1974 |
| GB | 1457098 | 12/1976 |
| GB | 1513777 | 6/1978 |
| GB | 1521413 | 8/1978 |
| GB | 2162147 | 1/1986 |
| GB | 2394416 | 4/2004 |
| GB | 2395124 | 5/2004 |
| GB | 2396107 | 6/2004 |
| GB | 2406053 | 3/2005 |
| IN | 7201/DELNP/2006 | 5/2005 |
| IN | 5081/DELNP/2008 | 8/2006 |
| JP | S 54-32636 | 3/1979 |
| JP | 55-064736 | 5/1980 |
| JP | 56-73005 | 6/1981 |
| JP | 1981-56184 | 6/1981 |
| JP | 1981-56187 | 6/1981 |
| JP | 1981-561932 | 6/1981 |
| JP | 60-146803 | 1/1984 |
| JP | 1985-047717 | 1/1985 |
| JP | S 60-146803 | 8/1985 |
| JP | 1986-052832 | 1/1986 |
| JP | 1986-207139 | 6/1986 |
| JP | 62-294079 | 12/1987 |
| JP | S 63-299449 | 6/1988 |
| JP | 1990-214404 | 6/1990 |
| JP | 1992-045981 | 12/1991 |
| JP | 93-216621 | 6/1993 |
| JP | H 05-139924 | 6/1993 |
| JP | H 05-236941 | 9/1993 |
| JP | 6-116111 | 4/1994 |
| JP | H 06-239715 | 8/1994 |
| JP | 07-501327 | 2/1995 |
| JP | 08-243378 | 9/1996 |
| JP | 09-067205 | 3/1997 |
| JP | 10-76155 | 3/1998 |
| JP | 10-164986 | 6/1998 |
| JP | 03-212497 | 8/1998 |
| JP | 10-338630 | 12/1998 |
| JP | 1997-114787 | 12/1998 |
| JP | 2000-053923 | 2/2000 |
| JP | 2004-24042 | 2/2000 |
| JP | 2000-139051 | 5/2000 |

(56) References Cited

FOREIGN PATENT DOCUMENTS

| | | |
|---|---|---|
| JP | 2000-351987 | 12/2000 |
| JP | 2000-44878 | 8/2001 |
| JP | 2001-294505 | 10/2001 |
| JP | 2001-316214 | 11/2001 |
| JP | 2002-262398 | 11/2001 |
| JP | 02-027903 | 1/2002 |
| JP | 2002-501007 | 1/2002 |
| JP | 2002-521406 | 7/2002 |
| JP | 02-067208 | 8/2002 |
| JP | 2003-002809 | 1/2003 |
| JP | 2003-507397 | 2/2003 |
| JP | 2003-529539 | 10/2003 |
| JP | 2003-531246 | 10/2003 |
| JP | 2003-534355 | 11/2003 |
| JP | 2005-513053 | 5/2005 |
| JP | 2005-200315 | 7/2005 |
| JP | 2008-542816 | 8/2006 |
| JP | 2008-542817 | 8/2006 |
| JP | 2007-502860 | 2/2007 |
| JP | 2007-538062 | 12/2007 |
| JP | 02-191961 | 6/2010 |
| MX | MX/a/2004/001906 | 3/2005 |
| MX | MX/a/2006/013420 | 8/2006 |
| MX | MX/a/2008/0006927 | 8/2006 |
| NZ | 531492 | 8/2002 |
| NZ | 551644 | 5/2005 |
| PH | 12006502324 | 5/2005 |
| WO | WO 2016/124927 | 8/1916 |
| WO | WO 1992/010946 | 9/1990 |
| WO | WO 1991/010772 | 7/1991 |
| WO | WO 1991/017741 | 11/1991 |
| WO | WO 92/07064 | 4/1992 |
| WO | WO 1994/009653 | 5/1994 |
| WO | WO 1996/036433 | 12/1996 |
| WO | WO 1996/038055 | 12/1996 |
| WO | WO 1997/047288 | 12/1997 |
| WO | WO 98/56340 | 12/1998 |
| WO | WO 1998/056340 | 12/1998 |
| WO | WO 99/30691 | 6/1999 |
| WO | WO 1999/030691 | 6/1999 |
| WO | WO 1999/037148 | 7/1999 |
| WO | WO 2000/005964 | 2/2000 |
| WO | WO 2000/010392 | 3/2000 |
| WO | WO 2000/021364 | 4/2000 |
| WO | WO 2000/049865 | 8/2000 |
| WO | WO 2000/051435 | 9/2000 |
| WO | WO 2000/051436 | 9/2000 |
| WO | WO 2000/053020 | 9/2000 |
| WO | WO 2001/011006 | 2/2001 |
| WO | WO 01/13726 | 3/2001 |
| WO | WO 2001/013727 | 3/2001 |
| WO | WO 2001/060163 | 8/2001 |
| WO | WO 2001/091555 | 12/2001 |
| WO | WO 2002/002213 | 1/2002 |
| WO | WO 2002/012348 | 2/2002 |
| WO | WO 2002/024259 | 3/2002 |
| WO | WO 2002/056879 | 7/2002 |
| WO | WO 2002/085314 | 10/2002 |
| WO | WO 2003/020024 | 3/2003 |
| WO | WO 2003/028451 | 4/2003 |
| WO | WO 2003/041509 | 5/2003 |
| WO | WO 2003/051121 | 6/2003 |
| WO | WO 2003/069993 | 8/2003 |
| WO | WO 2003/070286 | 8/2003 |
| WO | WO 2003/089561 | 10/2003 |
| WO | WO 2004/006679 | 1/2004 |
| WO | WO 2004/034791 | 4/2004 |
| WO | WO 2004/037004 | 5/2004 |
| WO | WO 2004/037232 | 5/2004 |
| WO | WO 2004/045588 | 6/2004 |
| WO | WO 2004/084947 | 10/2004 |
| WO | WO 2004/100971 | 11/2004 |
| WO | WO 2005/067733 | 7/2005 |
| WO | WO 2005/070213 | 8/2005 |
| WO | WO 2005/102045 | 11/2005 |
| WO | WO 2005/102508 | 11/2005 |
| WO | WO 2005/104842 | 11/2005 |
| WO | WO 2005/113128 | 12/2005 |
| WO | WO 2005113128 A1 * | 12/2005 ............. A01N 25/26 |
| WO | WO 2006/007372 | 1/2006 |
| WO | WO 2006/077568 | 7/2006 |
| WO | WO 2006/100308 | 9/2006 |
| WO | WO 2007/063267 | 6/2007 |
| WO | WO 2007/063268 | 6/2007 |
| WO | WO 2009/013361 | 1/2009 |
| WO | WO 2010/101821 | 9/2010 |
| WO | WO 2014/080199 | 5/2014 |
| WO | WO 2015/075409 | 5/2015 |
| ZA | 200402367 | 8/2005 |
| ZA | 200610427 | 1/2008 |

OTHER PUBLICATIONS

U.S. Appl. No. 14/188,790 (2014/0170198), filed Feb. 25, 2014 (Jun. 19, 2014), Lanny Franklin.
U.S. Appl. No. 15/037,187 (2016/0278367), filed May 17, 2016 (Sep. 29, 2016), Alexander John Abrey.
U.S. Appl. No. 15/547,503, filed Jul. 30, 2017, Alexander John Abrey.
U.S. Appl. No. 15/458,197 (2017/0245497), filed Mar. 14, 2017 (Aug. 31, 2017), Lanny Franklin.
U.S. Appl. No. 60/315,163, filed Aug. 28, 2001, Lanny Franklin.
U.S. Appl. No. 60/388,057, filed Jun. 11, 2002, Lanny Franklin.
U.S. Appl. No. 60/538,627, filed Jan. 23, 2004, Lanny Franklin.
U.S. Appl. No. 60/572,804, filed May 20, 2004, Lanny Franklin.
U.S. Appl. No. 60/572,892, filed May 20, 2004, Lanny Franklin.
U.S. Appl. No. 60/741,129, filed Nov. 30, 2005, Lanny Franklin.
U.S. Appl. No. 60/741,167, filed Nov. 30, 2005, Lanny Franklin.
PCT/GB2016/050254 (WO 2016/124927), Feb. 3, 2016 (Aug. 11, 2016), Alexander John Abrey.
PCT/US2002/02751 (WO 2003/020024), Aug. 28, 2002 (Mar. 13, 2003), Lanny Franklin.
PCT/GB2005/000240 (WO 2005/070213), Jan. 24, 2005 (Aug. 4, 2005), Lanny Franklin.
PCT/GB2005/002011 (WO 2005/113128), May 20, 2005 (Dec. 1, 2005), Lanny Franklin.
PCT/GB2006/002878 (WO 2007/063267), Aug. 3, 2006 (Jun. 7, 2007), Gary Ostroff.
PCT/GB2006/002881 (WO 2007/063268), Aug. 3, 2006 (Jun. 7, 2007), Gary Ostroff.
PCT/GB2013/053076 (WO 2015/075409), Nov. 21, 2013 (May 28, 2015), Alexander John Abrey.
U.S. Appl. No. 07/166,929, James, filed Mar. 11, 1998.
U.S. Appl. No. 60/741,167, Franklin, filed Nov. 30, 2005.
U.S. Appl. No. 60/741,129, Franklin, filed Nov. 30, 2005.
U.S. Appl. No. 60/572,892, Franklin, filed May 20, 2004.
U.S. Appl. No. 60/572,804, Franklin, filed May 20, 2004.
U.S. Appl. No. 60/538,627, Franklin, filed Jan. 23, 2004.
U.S. Appl. No. 60/388,057, Franklin, filed Jun. 11, 2002.
U.S. Appl. No. 60/315,163, Franklin, filed Aug. 28, 2001.
Preliminary Amendment filed on Jul. 19, 2006 for U.S. Appl. No. 10/586,597, filed Apr. 4, 2008 (Inventor—Lanny Franklin // Applicant—Eden Research PLC) (13 pages).
Restriction Requirement dated Jun. 18, 2010 for U.S. Appl. No. 10/586,597, filed Apr. 4, 2008 (Inventor—Lanny Franklin // Applicant—Eden Research PLC) (8 pages).
Response to Restriction Requirement filed on Jul. 19, 2010 for U.S. Appl. No. 10/586,597, filed Apr. 4, 2008 (Inventor—Lanny Franklin // Applicant—Eden Research PLC) (13 pages).
Examiner Interview Summary dated Jul. 26, 2010 for U.S. Appl. No. 10/586,597, filed Apr. 4, 2008 (Inventor—Lanny Franklin // Applicant—Eden Research PLC) (3 pages).
Non-Final Office Action dated Oct. 15, 2010 for U.S. Appl. No. 10/586,597, filed Apr. 4, 2008 (Inventor—Lanny Franklin // Applicant—Eden Research PLC) (12 pages).
Response to Non-Final Office Action filed on Feb. 15, 2011 for U.S. Appl. No. 10/586,597, filed Apr. 4, 2008 (Inventor—Lanny Franklin // Applicant—Eden Research PLC) (20 pages).

(56) References Cited

OTHER PUBLICATIONS

Final Office Action dated Apr. 8, 2011 for U.S. Appl. No. 10/586,597, filed Apr. 4, 2008 (Inventor—Lanny Franklin // Applicant—Eden Research PLC) (12 pages).
Response to Final Office Action filed on Oct. 18, 2011 for U.S. Appl. No. 10/586,597, filed Apr. 4, 2008 (Inventor—Lanny Franklin // Applicant—Eden Research PLC) (18 pages).
1.132 Declaration filed on Oct. 18, 2011 for U.S. Appl. No. 10/586,597, filed Apr. 4, 2008 (Inventor—Lanny Franklin // Applicant—Eden Research PLC) (22 pages).
Non-Final Office Action dated May 30, 2013 for U.S. Appl. No. 10/586,597, filed Apr. 4, 2008 (Inventor—Lanny Franklin // Applicant—Eden Research PLC) (13 pages).
Response to Non-Final Office Action filed on Dec. 2, 2013 for U.S. Appl. No. 10/586,597, filed Apr. 4, 2008 (Inventor—Lanny Franklin // Applicant—Eden Research PLC) (23 pages).
Final Office Action dated Dec. 17, 2013 for U.S. Appl. No. 10/586,597, filed Apr. 4, 2008 (Inventor—Lanny Franklin // Applicant—Eden Research PLC) (10 pages).
Response to Final Office Action filed May 19, 2014 for U.S. Appl. No. 10/586,597, filed Apr. 4, 2008 (Inventor—Lanny Franklin // Applicant—Eden Research PLC) (17 pages).
Non-Final Office Action dated Oct. 6, 2014 for U.S. Appl. No. 10/586,597, filed Apr. 4, 2008 (Inventor—Lanny Franklin // Applicant—Eden Research PLC) (15 pages).
Response to Office Action filed Apr. 6, 2015 for U.S. Appl. No. 10/586,597, filed Apr. 4, 2008 (Inventor—Lanny Franklin // Applicant—Eden Research PLC) (16 pages).
Notice of Non-Compliant Amendment dated Apr. 21, 2015 for U.S. Appl. No. 10/586,597, filed Apr. 4, 2008 (Inventor—Lanny Franklin // Applicant—Eden Research PLC) (3 pages).
Response to Notice of Non-Compliant Amendment filed Jun. 10, 2015 for U.S. Appl. No. 10/586,597, filed Apr. 4, 2008 (Inventor—Lanny Franklin // Applicant—Eden Research PLC) (7 pages).
Final Office Action dated Sep. 2, 2015 for U.S. Appl. No. 10/586,597, filed Apr. 4, 2008 (Inventor—Lanny Franklin // Applicant—Eden Research PLC) (17 pages).
Response to Office Action filed Mar. 2, 2016 for U.S. Appl. No. 10/586,597, filed Apr. 4, 2008 (Inventor—Lanny Franklin // Applicant—Eden Research PLC) (19 pages).
Non-Final Office Action dated Mar. 24, 2016 for U.S. Appl. No. 10/586,597, filed Apr. 4, 2008 (Inventor—Lanny Franklin // Applicant—Eden Research PLC) (17 pages).
Response to Non-Final Office Action filed Sep. 24, 2016 for U.S. Appl. No. 10/586,597, filed Apr. 4, 2008 (Inventor—Lanny Franklin // Applicant—Eden Research PLC) (15 pages).
Notice of Allowance dated Dec. 9, 2016 for U.S. Appl. No. 10/586,597, filed Apr. 4, 2008 (Inventor—Lanny Franklin // Applicant—Eden Research PLC) (8 pages).
Rule 1.312 Amendment filed Mar. 8, 2017 for U.S. Appl. No. 10/586,597, filed Apr. 4, 2008 (Inventor—Lanny Franklin // Applicant—Eden Research PLC) (3 pages).
Corrected Noticed of Allowability dated Apr. 26, 2017 for U.S. Appl. No. 10/586,597, filed Apr. 4, 2008 (Inventor—Lanny Franklin // Applicant—Eden Research PLC) (4 pages).
Issue Notification dated May 3, 2017 for U.S. Appl. No. 10/586,597, filed Apr. 4, 2008 (Inventor—Lanny Franklin // Applicant—Eden Research PLC) (1 page).
Preliminary Amendment filed Mar. 14, 2017 for U.S. Appl. No. 15/458,197, filed Mar. 14, 2007 (Inventor—Lanny Franklin // Applicant—Eden Research PLC) (3 pages).
Notice to File Missing Parts dated Mar. 22, 2017 for U.S. Appl. No. 15/458,197, filed Mar. 14, 2007 (Inventor—Lanny Franklin // Applicant—Eden Research PLC) (2 pages).
Response to Notice to File Missing Parts filed May 22, 2017 for U.S. Appl. No. 15/458,197, filed Mar. 14, 2007 (Inventor—Lanny Franklin // Applicant—Eden Research PLC) (2 pages).
Non-Final Office Action dated Oct. 19, 2007 for U.S. Appl. No. 15/458,197, filed Mar. 14, 2007 (Inventor—Lanny Franklin // Applicant—Eden Research PLC) (8 pages).
Preliminary Amendment filed Nov. 20, 2006 for U.S. Appl. No. 11/597,116, filed Oct. 27, 2008 (Inventor—Lanny Franklin // Applicant—Eden Research PLC) (14 pages).
Restriction Requirement dated Apr. 26, 2011 for U.S. Appl. No. 11/597,116, filed Oct. 27, 2008 (Inventor—Lanny Franklin // Applicant—Eden Research PLC) (8 pages).
Response to Restriction Requirement filed Jun. 27, 2011 for U.S. Appl. No. 11/597,116, filed Oct. 27, 2008 (Inventor—Lanny Franklin // Applicant—Eden Research PLC) (14 pages).
Non-Final Office Action dated Dec. 13, 2011 for U.S. Appl. No. 11/597,116, filed Oct. 27, 2008 (Inventor—Lanny Franklin // Applicant—Eden Research PLC) (15 pages).
Response to Non-Final Office Action filed Apr. 13, 2012 for U.S. Appl. No. 11/597,116, filed Oct. 27, 2008 (Inventor—Lanny Franklin // Applicant—Eden Research PLC) (18 pages).
Non-Final Office Action dated Jul. 12, 2012 for U.S. Appl. No. 11/597,116, filed Oct. 27, 2008 (Inventor—Lanny Franklin // Applicant—Eden Research PLC) (18 pages).
Response to Non-Final Office Action filed Oct. 12, 2012 for U.S. Appl. No. 11/597,116, filed Oct. 27, 2008 (Inventor—Lanny Franklin // Applicant—Eden Research PLC) (19 pages).
Non-Final Office Action dated Jun. 18, 2013 for U.S. Appl. No. 11/597,116, filed Oct. 27, 2008 (Inventor—Lanny Franklin // Applicant—Eden Research PLC) (22 pages).
Response to Non-Final Office Action filed Nov. 18, 2013 for U.S. Appl. No. 11/597,116, filed Oct. 27, 2008 (Inventor—Lanny Franklin // Applicant—Eden Research PLC) (19 pages).
Final Office Action dated Dec. 19, 2013 for U.S. Appl. No. 11/597,116, filed Oct. 27, 2008 (Inventor—Lanny Franklin // Applicant—Eden Research PLC) (24 pages).
Response to Final Office Action filed Jun. 19, 2014 for U.S. Appl. No. 11/597,116, filed Oct. 27, 2008 (Inventor—Lanny Franklin // Applicant—Eden Research PLC) (16 pages).
Final Office Action dated Dec. 17, 2014 for U.S. Appl. No. 11/597,116, filed Oct. 27, 2008 (Inventor—Lanny Franklin // Applicant—Eden Research PLC) (18 pages).
Response to Office Action filed Jun. 17, 2015 for U.S. Appl. No. 11/597,116, filed Oct. 27, 2008 (Inventor—Lanny Franklin // Applicant—Eden Research PLC) (17 pages).
Final Office Action dated Sep. 11, 2015 for U.S. Appl. No. 11/597,116, filed Oct. 27, 2008 (Inventor—Lanny Franklin // Applicant—Eden Research PLC) (19 pages).
Response to Office Action filed Mar. 10, 2016 for U.S. Appl. No. 11/597,116, filed Oct. 27, 2008 (Inventor—Lanny Franklin // Applicant—Eden Research PLC) (18 pages).
Non-Final Office Action dated Dec. 30, 2016 for U.S. Appl. No. 11/597,116, filed Oct. 27, 2008 (Inventor—Lanny Franklin // Applicant—Eden Research PLC) (25 pages).
Response to Non-Final Office Action filed Mar. 30, 2017 for U.S. Appl. No. 11/597,116, filed Oct. 27, 2008 (Inventor—Lanny Franklin // Applicant—Eden Research PLC) (21 pages).
Final Office Action dated May 5, 2017 for U.S. Appl. No. 11/597,116, filed Oct. 27, 2008 (Inventor—Lanny Franklin // Applicant—Eden Research PLC) (27 pages).
Response to Final Office Action pursuant to AFCP 2.0 filed Aug. 17, 2017 for U.S. Appl. No. 11/597,116, filed Oct. 27, 2008 (Inventor—Lanny Franklin // Applicant—Eden Research PLC) (29 pages).
Decision to AFCP 2.0 Request dated Sep. 21, 2017 for U.S. Appl. No. 11/597,116, filed Oct. 27, 2008 (Inventor—Lanny Franklin // Applicant—Eden Research PLC) (6 pages).
Response to Final Office Action filed Nov. 6, 2017 for U.S. Appl. No. 11/597,116, filed Oct. 27, 2008 (Inventor—Lanny Franklin // Applicant—Eden Research PLC) (28 pages).
1.132 Declaration filed Nov. 6, 2017 for U.S. Appl. No. 11/597,116, filed Oct. 27, 2008 (Inventor—Lanny Franklin // Applicant—Eden Research PLC) (9 pages).
Preliminary Amendment filed May 30, 2008 for U.S. Appl. No. 12/095,584, filed Aug. 28, 2009 (Inventor—Lanny Franklin // Applicant—Eden Research PLC) (7 pages).
Non-Final Office Action dated Oct. 7, 2011 for U.S. Appl. No. 12/095,584, filed Aug. 28, 2009 (Inventor—Lanny Franklin // Applicant—Eden Research PLC) (15 pages).

(56) References Cited

OTHER PUBLICATIONS

Response to Non-Final Office Action filed Mar. 5, 2012 for U.S. Appl. No. 12/095,584, filed Aug. 28, 2009 (Inventor—Lanny Franklin // Applicant—Eden Research PLC) (21 pages).
Final Office Action dated Apr. 17, 2012 for U.S. Appl. No. 12/095,584, filed Aug. 28, 2009 (Inventor—Lanny Franklin // Applicant—Eden Research PLC) (19 pages).
Response to Final Office Action filed Sep. 17, 2012 for U.S. Appl. No. 12/095,584, filed Aug. 28, 2009 (Inventor—Lanny Franklin // Applicant—Eden Research PLC) (23 pages).
Final Office Action dated Nov. 5, 2013 for U.S. Appl. No. 12/095,584, filed Aug. 28, 2009 (Inventor—Lanny Franklin // Applicant—Eden Research PLC) (22 pages).
Response to Office Action filed May 4, 2014 for U.S. Appl. No. 12/095,584, filed Aug. 28, 2009 (Inventor—Lanny Franklin // Applicant—Eden Research PLC) (27 pages).
Final Office Action dated Jul. 8, 2014 for U.S. Appl. No. 12/095,584, filed Aug. 28, 2009 (Inventor—Lanny Franklin // Applicant—Eden Research PLC) (20 pages).
Response to Office Action filed Jan. 8, 2015 for U.S. Appl. No. 12/095,584, filed Aug. 28, 2009 (Inventor—Lanny Franklin // Applicant—Eden Research PLC) (22 pages).
Final Office Action dated Feb. 13, 2015 for U.S. Appl. No. 12/095,584, filed Aug. 28, 2009 (Inventor—Lanny Franklin // Applicant—Eden Research PLC) (19 pages).
Response to Office Action filed Aug. 13, 2015 for U.S. Appl. No. 12/095,584, filed Aug. 28, 2009 (Inventor—Lanny Franklin // Applicant—Eden Research PLC) (17 pages).
Supplemental Response to Office Action filed Sep. 4, 2015 for U.S. Appl. No. 12/095,584, filed Aug. 28, 2009 (Inventor—Lanny Franklin // Applicant—Eden Research PLC) (14 pages).
Non-Final Office Action dated Sep. 25, 2015 for U.S. Appl. No. 12/095,584, filed Aug. 28, 2009 (Inventor—Lanny Franklin // Applicant—Eden Research PLC) (23 pages).
Response to Office Action filed Mar. 25, 2016 for U.S. Appl. No. 12/095,584, filed Aug. 28, 2009 (Inventor—Lanny Franklin // Applicant—Eden Research PLC) (25 pages).
Final Office Action dated Apr. 26, 2016 for U.S. Appl. No. 12/095,584, filed Aug. 28, 2009 (Inventor—Lanny Franklin // Applicant—Eden Research PLC) (27 pages).
Response to Final Office Action filed Oct. 26, 2016 for U.S. Appl. No. 12/095,584, filed Aug. 28, 2009 (Inventor—Lanny Franklin // Applicant—Eden Research PLC) (24 pages).
Final Office Action dated Nov. 22, 2016 for U.S. Appl. No. 12/095,584, filed Aug. 28, 2009 (Inventor—Lanny Franklin // Applicant—Eden Research PLC) (30 pages).
Interview Summary dated Mar. 7, 2017 for U.S. Appl. No. 12/095,584, filed Aug. 28, 2009 (Inventor—Lanny Franklin // Applicant—Eden Research PLC) (3 pages).
After Final Response with AFCP 2.0 Request filed Mar. 22, 2017 for U.S. Appl. No. 12/095,584, filed Aug. 28, 2009 (Inventor—Lanny Franklin // Applicant—Eden Research PLC) (21 pages).
Advisory Action dated Apr. 4, 2017 for U.S. Appl. No. 12/095,584, filed Aug. 28, 2009 (Inventor—Lanny Franklin // Applicant—Eden Research PLC) (5 pages).
Preliminary Amendment filed May 30, 2008 for U.S. Appl. No. 12/095,580, filed Jul. 22, 2009 (Inventor—Lanny Franklin // Applicant—Eden Research PLC) (11 pages).
Restriction Requirement dated Jun. 24, 2011 for U.S. Appl. No. 12/095,580, filed Jul. 22, 2009 (Inventor—Lanny Franklin // Applicant—Eden Research PLC) (15 pages).
Response to Restriction Requirement filed Oct. 24, 2011 for U.S. Appl. No. 12/095,580, filed Jul. 22, 2009 (Inventor—Lanny Franklin // Applicant—Eden Research PLC) (12 pages).
Non-Final Office Action dated Dec. 22, 2011 for U.S. Appl. No. 12/095,580, filed Jul. 22, 2009 (Inventor—Lanny Franklin // Applicant—Eden Research PLC) (15 pages).
Response to Non-Final Office Action filed Mar. 22, 2012 for U.S. Appl. No. 12/095,580, filed Jul. 22, 2009 (Inventor—Lanny Franklin // Applicant—Eden Research PLC) (16 pages).
Final Office Action dated Jul. 25, 2012 for U.S. Appl. No. 12/095,580, filed Jul. 22, 2009 (Inventor—Lanny Franklin // Applicant—Eden Research PLC) (20 pages).
Response to Final Office Action filed Oct. 24, 2012 for U.S. Appl. No. 12/095,580, filed Jul. 22, 2009 (Inventor—Lanny Franklin // Applicant—Eden Research PLC) (22 pages).
Non-Final Office Action dated Jun. 6, 2013 for U.S. Appl. No. 12/095,580, filed Jul. 22, 2009 (Inventor—Lanny Franklin // Applicant—Eden Research PLC) (24 pages).
Response to Non-Final Office Action filed Sep. 6, 2013 for U.S. Appl. No. 12/095,580, filed Jul. 22, 2009 (Inventor—Lanny Franklin // Applicant—Eden Research PLC) (19 pages).
Final Office Action dated Oct. 2, 2013 for U.S. Appl. No. 12/095,580, filed Jul. 22, 2009 (Inventor—Lanny Franklin // Applicant—Eden Research PLC) (24 pages).
Response to Final Office Action filed Mar. 3, 2014 for U.S. Appl. No. 12/095,580, filed Jul. 22, 2009 (Inventor—Lanny Franklin // Applicant—Eden Research PLC) (17 pages).
Non-Final Office Action dated Apr. 9, 2014 for U.S. Appl. No. 12/095,580, filed Jul. 22, 2009 (Inventor—Lanny Franklin // Applicant—Eden Research PLC) (30 pages).
Interview Summary dated Jul. 22, 2014 for U.S. Appl. No. 12/095,580, filed Jul. 22, 2009 (Inventor—Lanny Franklin // Applicant—Eden Research PLC) (3 pages).
Response to Non-Final Office Action filed Sep. 9, 2014 for U.S. Appl. No. 12/095,580, filed Jul. 23, 2009 (Inventor—Lanny Franklin // Applicant—Eden Research PLC) (15 pages).
Final Office Action dated Jan. 7, 2015 for U.S. Appl. No. 12/095,580, filed Jul. 23, 2009 (Inventor—Lanny Franklin // Applicant—Eden Research PLC) (25 pages).
Response to Final Office Action filed Jul. 7, 2015 for U.S. Appl. No. 12/095,580, filed Jul. 23, 2009 (Inventor—Lanny Franklin // Applicant—Eden Research PLC) (26 pages).
Non-Final Office Action dated Jul. 30, 2015 for U.S. Appl. No. 12/095,580, filed Jul. 23, 2009 (Inventor—Lanny Franklin // Applicant—Eden Research PLC) (27 pages).
Response to Non-Final Office Action filed Feb. 1, 2016 for U.S. Appl. No. 12/095,580, filed Jul. 23, 2009 (Inventor—Lanny Franklin // Applicant—Eden Research PLC) (24 pages).
Notice of Allowance dated May 4, 2016 for U.S. Appl. No. 12/095,580, filed Jul. 23, 2009 (Inventor—Lanny Franklin // Applicant—Eden Research PLC) (11 pages).
Notice to File Corrected Application Papers dated May 27, 2016 for U.S. Appl. No. 12/095,580, filed Jul. 23, 2009 (Inventor—Lanny Franklin // Applicant—Eden Research PLC) (3 pages).
Rule 1.312 Amendment filed Jun. 7, 2016 for U.S. Appl. No. 12/095,580, filed Jul. 23, 2009 (Inventor—Lanny Franklin // Applicant—Eden Research PLC) (4 pages).
Response to Rule 1.312 Amendment dated Jun. 10, 2016 for U.S. Appl. No. 12/095,580, filed Jul. 23, 2009 (Inventor—Lanny Franklin // Applicant—Eden Research PLC) (2 pages).
Rule 1.312 Amendment filed Jul. 6, 2016 for U.S. Appl. No. 12/095,580, filed Jul. 23, 2009 (Inventor—Lanny Franklin // Applicant—Eden Research PLC) (5 pages).
Rule 1.312 Amendment filed Jul. 6, 2016 for U.S. Appl. No. 12/095,580, filed Jul. 23, 2009 (Inventor—Lanny Franklin // Applicant—Eden Research PLC) (4 pages).
Communication re: Rule 1.312 Amendment issued Aug. 1, 2016 for U.S. Appl. No. 12/095,580, filed Jul. 23, 2009 (Inventor—Lanny Franklin // Applicant—Eden Research PLC) (7 pages).
Issue Notification dated Aug. 24, 2016 for U.S. App. No. 12/095,580, filed Jul. 23, 2009 (Inventor—Lanny Franklin // Applicant—Eden Research PLC) (1 page).
Preliminary Amendment filed Feb. 25, 2014 for U.S. Appl. No. 14/188,790, filed Feb. 25, 2014 (Inventor—Lanny Franklin // Applicant—Eden Research PLC) (6 pages).
Non-Final Office Action dated Jul. 14, 2015 for U.S. Appl. No. 14/188,790, filed Feb. 25, 2014 (Inventor—Lanny Franklin // Applicant—Eden Research PLC) (15 pages).
Response to Office Action filed Jan. 13, 2016 for U.S. Appl. No. 14/188,790, filed Feb. 25, 2014 (Inventor—Lanny Franklin // Applicant—Eden Research PLC) (17 pages).

(56) References Cited

OTHER PUBLICATIONS

Final Office Action dated Mar. 16, 2016 for U.S. Appl. No. 14/188,790, filed Feb. 25, 2014 (Inventor—Lanny Franklin // Applicant—Eden Research PLC) (24 pages).
Non-Final Office Action dated Oct. 3, 2016 for U.S. Appl. No. 14/188,790, filed Feb. 25, 2014 (Inventor—Lanny Franklin // Applicant—Eden Research PLC) (22 pages).
Response to Office Action filed Feb. 3, 2017 for U.S. Appl. No. 14/188,790, filed Feb. 25, 2014 (Inventor—Lanny Franklin // Applicant—Eden Research PLC) (18 pages).
Final Office Action dated May 12, 2017 for U.S. Appl. No. 14/188,790, filed Feb. 25, 2014 (Inventor—Lanny Franklin // Applicant—Eden Research PLC) (21 pages).
Response to Final Office Action filed Nov. 13, 2017 for U.S. Appl. No. 14/188,790, filed Feb. 25, 2014 (Inventor—Lanny Franklin // Applicant—Eden Research PLC) (20 pages).
Declaration pursuant to 37 C.F.R. § 1.132 filed Nov. 13, 2017 for U.S. Appl. No. 14/188,790, filed Feb. 25, 2014 (Inventor—Lanny Franklin // Applicant—Eden Research PLC) (9 pages).
Preliminary Amendment filed May 17, 2016 for U.S. Appl. No. 15/037,187, filed May 17, 2016 (Inventor—Lanny Franklin // Applicant—Eden Research PLC) (7 pages).
Species Election Requirement issued Mar. 28, 2017 for U.S. Appl. No. 15/037,187, filed May 17, 2016 (Inventor—Lanny Franklin // Applicant—Eden Research PLC) (8 pages).
Response to Species Election Requirement filed May 26, 2017 for U.S. Appl. No. 15/037,187, filed May 17, 2016 (Inventor—Lanny Franklin // Applicant—Eden Research PLC) (5 pages).
Non-Final Office Action dated Oct. 3, 2017 for U.S. Appl. No. 15/037,187, filed May 17, 2016 (Inventor—Lanny Franklin // Applicant—Eden Research PLC) (14 pages).
Preliminary Amendment filed Jul. 30, 2017 for U.S. Appl. No. 15/547,503, filed Jul. 30, 2017 (Inventor—Alexander Abrey // Applicant—Eden Research PLC) (4 pages).
Second Preliminary Amendment filed Nov. 30, 2017 for U.S. Appl. No. 15/547,503, filed Jul. 30, 2017 (Inventor—Alexander Abrey // Applicant—Eden Research PLC) (7 pages).
Preliminary Amendment filed Feb. 27, 2004 for U.S. Appl. No. 10/488,130, filed Jul. 7, 2004 (Inventor—Lanny Franklin // Applicant—Eden Research PLC) (7 Pages).
Non-Final Office Action dated May 17, 2006 for U.S. Appl. No. 10/488,130, filed Jul. 7, 2004 (Inventor—Lanny Franklin // Applicant—Eden Research PLC) (12 Pages).
Response for Non-Final Office Action filed Sep. 18, 2006 for U.S. Appl. No. 10/488,130, filed Jul. 7, 2004 (Inventor—Lanny Franklin // Applicant—Eden Research PLC) (9 Pages).
Final Office Action dated Nov. 30, 2006 for U.S. Appl. No. 10/488,130, filed Jul. 7, 2004 (Inventor—Lanny Franklin // Applicant—Eden Research PLC) (6 Pages).
Response to Final Office Action filed May 24, 2007 for U.S. Appl. No. 10/488,130, filed Jul. 7, 2004 (Inventor—Lanny Franklin // Applicant—Eden Research PLC) (14 Pages).
Non-Final Office Action dated Mar. 4, 2008 for U.S. Appl. No. 10/488,130, filed Jul. 7, 2004 (Inventor—Lanny Franklin // Applicant—Eden Research PLC) (10 Pages).
Response for Non-Final Office Action filed Aug. 21, 2008 for U.S. Appl. No. 10/488,130, filed Jul. 7, 2004 (Inventor—Lanny Franklin // Applicant—Eden Research PLC) (15 Pages).
1.132 Declaration filed Aug. 21, 2008 for U.S. Appl. No. 10/488,130, filed Jul. 7, 2004 (Inventor—Lanny Franklin // Applicant—Eden Research PLC) (21 Pages).
Non-Final Office Action dated Dec. 5, 2008 for U.S. Appl. No. 10/488,130, filed Jul. 7, 2004 (Inventor—Lanny Franklin // Applicant—Eden Research PLC) (8 Pages).
Interview Summary dated Jul. 8, 2009 for U.S. Appl. No. 10/488,130, filed Jul. 7, 2004 (Inventor—Lanny Franklin // Applicant—Eden Research PLC) (3 Pages).
International Preliminary Report on Patentability dated Jun. 3, 2008 for Int'l. Patent Application PCT/GB2006/002878 filed Aug. 3, 2006 and published as WO 2007/063267 dated Jun. 7, 2002 (Inventor—Lanny Franklin // Applicant—Eden Research PLC) (7 pages).
International Search Report dated Nov. 21, 2006 for Int'l. Patent Application PCT/GB2006/002878 filed Aug. 3, 2006 and published as WO 2007/063267 dated Jun. 7, 2002 (Inventor—Lanny Franklin // Applicant—Eden Research PLC) (4 pages).
Written Opinion dated May 31, 2008 for Int'l. Patent Application PCT/GB2006/002878 filed Aug. 3, 2006 and published as WO 2007/063267 dated Jun. 7, 2002 (Inventor—Lanny Franklin // Applicant—Eden Research PLC) (6 pages).
International Search Report dated Sep. 15, 2005 for Int'l. Patent Application PCT/GB/2005/000240 filed Jan. 24, 2005 and published as WO 2005/070213 dated Aug. 4, 2005 (Inventor—Lanny Franklin // Applicant—Eden Research PLC) (6 pages).
Written Opinion dated Jul. 24, 2006 for Int'l. Patent Application PCT/GB/2005/000240 filed Jan. 24, 2005 and published as WO 2005/070213 dated Aug. 4, 2005 (Inventor—Lanny Franklin // Applicant—Eden Research PLC) (8 pages).
International Preliminary Report on Patentability dated Jul. 24, 2006 for Int'l. Patent Application PCT/GB/2005/000240 filed Jan. 24, 2005 and published as WO 2005/070213 dated Aug. 4, 2005 (Inventor—Lanny Franklin // Applicant—Eden Research PLC) (9 pages).
International Search Report dated May 15, 2003 for Int'l. Patent Application PCT/US02/27512 filed Aug. 28, 2002 and published as WO 2003/020024 dated Mar. 13, 2003 (Inventor—Lanny Franklin // Applicant—Eden Research PLC) (4 pages).
International Preliminary Examination Report dated Jan. 14, 2005 for Int'l. Patent Application PCT/US02/27512 filed Aug. 28, 2002 and published as WO 2003/020024 dated Mar. 13, 2003 (Inventor—Lanny Franklin // Applicant—Eden Research PLC) (9 pages).
International Search Report dated Sep. 8, 2005 for Int'l. Patent Application PCT/GB2005/002011 filed May 20, 2005 and published as WO 2005/113128 dated Sep. 8, 2005 (Inventor—Lanny Franklin // Applicant—Eden Research PLC) (6 pages).
Written Opinion dated Sep. 6, 2005 for Int'l. Patent Application PCT/GB2005/002011 filed May 20, 2005 and published as WO 2005/113128 dated Nov. 20, 2006 (Inventor—Lanny Franklin // Applicant—Eden Research PLC) (9 pages).
International Preliminary Report on Patentability dated Nov. 26, 2006 for Int'l. Patent Application PCT/GB2005/002011 filed May 20, 2005 and published as WO 2005/113128 dated Nov. 21, 2006 (Inventor—Lanny Franklin // Applicant—Eden Research PLC) (10 pages).
International Search Report dated Nov. 27, 2006 for Int'l. Patent Application PCT/GB2006/002881 filed Aug. 3, 2006 and published as WO 2007/063268 dated Jun. 7, 2007 (Inventor—Lanny Franklin // Applicant—Eden Research PLC) (5 pages).
Written Opinion dated May 31, 2008 for Int'l. Patent Application PCT/GB2006/002881 filed Aug. 3, 2006 and published as WO 2007/063268 dated Jun. 7, 2007 (Inventor—Lanny Franklin // Applicant—Eden Research PLC) (10 pages).
International Preliminary Report on Patentability dated Jun. 3, 2008 for Int'l. Patent Application PCT/GB2006/002881 filed Aug. 3, 2006 and published as WO 2007/063268 dated Jun. 7, 2007 (Inventor—Lanny Franklin // Applicant—Eden Research PLC) (11 pages).
International Search Report dated Aug. 11, 2016 for Int'l. Patent Application PCT/GB2016/050254 filed Feb. 3, 2016 and published as WO 2016/124927 dated Aug. 11, 2016 (Inventor—Alexander John Abrey // Applicant—Eden Research PLC) (8 pages).
Written Opinion dated Aug. 11, 2016 for Int'l. Patent Application PCT/GB2016/050254 filed Feb. 3, 2016 and published as WO 2016/124927 dated Aug. 11, 2016 (Inventor—Alexander John Abrey // Applicant—Eden Research PLC) (9 pages).
International Preliminary Report on Patentability dated Aug. 11, 2016 for Int'l. Patent Application PCT/GB2016/050254 filed Feb. 3, 2016 and published as WO 2016/124927 dated Aug. 11, 2016 (Inventor—Alexander John Abrey // Applicant—Eden Research PLC) (10 pages).

(56) References Cited

OTHER PUBLICATIONS

International Preliminary Report on Patentability dated May 24, 2016 for Int'l. Patent Application PCT/GB2013/053076 filed Nov. 21, 2013 and published as WO 2015/075409 dated Nov. 21, 2013 (Inventor—Alexander John Abrey // Applicant—Eden Research PLC) (9 pages).
Written Opinion dated May 21, 2016 for Int'l. Patent Application PCT/GB2013/053076 filed Nov. 21, 2013 and published as WO 2015/075409 dated Nov. 21, 2013 (Inventor—Alexander John Abrey // Applicant—Eden Research PLC) (8 pages).
International Search Report dated May 28, 2015 for Int'l. Patent Application PCT/GB2013/053076 filed Nov. 21, 2013 and published as WO 2015/075409 dated Nov. 21, 2013 (Inventor—Alexander John Abrey // Applicant—Eden Research PLC) (4 pages).
Abegaz BM. (1991) Polyacetylenic thiophenes and terpenoids from the roots of Echinops pappii. Phytochemistry. 30(3): 879-881.
Abid M, et al. (1997) Nematicidal properties of *Stoechospermum marginatum*, a seaweed. Pakistan J Phytopathology. 9(2): 143-147.
Aikawa T, et al. (1998). An effect of pine volatiles on departure of Bursaphelenchus xylophilus (Nematoda: Aphelenchoididae) from Monochamus alternatus (Coleoptera: Cerambycidae). Appl. Entomol. Zool. 33(2): 231-237.
Akao N, et al. (1993) Changing chemosusceptibility in the second-stage larvae of Toxocara canis by long-term incubation. J Helminthol. 67(2): 145-150.
Andes D, et al. (2000) Report of successful prolonged antifungal therapy for refractory allergic fungal sinusitis. Clin Infect Dis. 31(1): 202-204.
Andrews RE, et al. (1980) Some effects of douglas fir terpenes on certain microorganisms. Appl Environ Microbiol. 40(2):301-304.
Arnold WN. (1981) Chapter 7. Lipids. Yeast Cell Envelopes: Biochemisry, Biophysics, and Ultrastructure. CRC Press. Boca Raton.
Arctander S. (1969). Perfume and flavor chemicals: (aroma chemicals) (vol. 2). Allured Publishing Corporation.
Asakawa Y. (2001). Recent advances in phytochemistry of bryophytes-acetogenins, terpenoids and bis (bibenzyl) s from selected Japanese, Taiwanese, New Zealand, Argentinean and European liverworts. Phytochemistry. 56(3): 297-312.
Author Unknown (1998) "Yeast—better a friend than foe!" Food Processing. 67(9): 15-18.
Bae EA, et al. (1998) Anti-Helicobacter pylori activity of herbal medicines. Biol Pharm Bull. 21(9): 990-992.
Bard M, et al. (1988) Geraniol interferes with membrane functions in strains of Candida and *Saccharomyces*. Lipids. 23(6):534-538.
Bauske EM, et al. (1994). Management of Meloidogyne incognita on cotton by use of botanical aromatic compounds. Nematropica. 24(2): 143-150.
Bauske EM, et al. (1997). Effect of botanical aromatic compounds and seed-surface pH on growth and colonization of cotton plant growth-promoting rhizobacteria. Biocontrol Sci Technol. 7(3): 415-421.
Biothera. (2008) Physical Properties and Specification Sheet for Wellmune wgp. (2 pages).
Bishop JR, et al. (1998) Microencapsulation in yeast cells. J Microencapsul. 15(6): 761-773.
Blagburn BL. (2000) Changing trends in ectoparasite control. Veterinary Dermatology. 11:5-5.
Board of Appeal of the European Patent Office. Datasheet for the Decision dated Jul. 9, 2009. Case No. T 0358/08 for Publication No. 1214034. Patentee is The Proctor & Gamble Company. (43 pages).
Borris RP, et al. (1992). Antiparasitic agents from plants. Phytochemical Resources for Medicine and Agriculture. Springer US. pp. 117-158.
Calvet C, et al. (2001) Evaluation of natural compounds against Root-lesion and rootknot nematodes and side effects on the ineffectivity of arbuscular mycorrhizal fungi. Eur J Plant Pathol. 107(6): 601-605.

Chaumont JP, et al. (1992). Campaign against allergenic moulds in dwellings. Inhibitor properties of essential oil of Geranium 'Bourbon', citronellol, geraniol and citral. Ann Pharm Fr. 50(3):156-166.
Chavarria-Carvajal JA. (1998). Use of organic amendments and naturally occurring aromatic compounds for control of plant-parasitic nematodes: Effects on microbial activity and soil enzymes (Meloidogyne incognita). 3397-3397.
Chitwood DJ. (1993). Naturally occurring nematicides. American Chemical Society (ACS). Washington. pp. 300-315.
Chitwood DJ. (2002) Phytochemical based strategies for nematode control. Annu Rev Phytopathol. 40: 221-249.
Crowell PL, et al. (1994) Chemoprevention and therapy of cancer by d-limonene. Crit Rev Oncog. 5(1):1-22.
Crowell PL, et al. (1996) Antitumorigenic effects of limonene and perillyl alcohol against pancreatic and breast cancer. Adv Exp Med Biol. 401: 131-136.
Deeley J, et al. (1979). Use of Dienes' stain to detect plant diseases induced by mycoplasmalike organisms. Phytopathology. 69(1): 169-1171.
Didry N, et al. (1994) Activity of thymol, carvacrol, cinnameldehyde and eugenol on oral bacteria. Pharm Acta Helv. 69(1): 25-28.
Dorman HJ, et al. (2000) Antimicrobial agents from plants: antibacterial activity of plant volatile oils. J Appl Microbiol. 88(2): 308-316.
Duke SO. (1991). Plant terpenoids as pesticides. Handbook of Natural Toxins. pp. 269-296.
Eden-Green SJ. (1982). Culture of other microorganisms from yellows-diseased plants. Plant and insect mycoplasma techniques. Springer Netherlands. 201-239.
Elegbede JA, et al. (1984) Inhibition of DMBA-induced mammary cancer by the monoterpene d-limonene. Carcinogenesis. 5(5): 661-664.
Elegbede JA, et al. (1986) Regression of rat primary mammary tumors following dietary d-limonene. J Natl Cancer Inst. 76(2): 323-325.
Elson CE, et al. (1994). The chemoprevention of cancer by mevalonate-derived constituents of fruits and vegetables. J Nutr. 124(5): 607-614.
Enwerem NM, et al. (2001). Anthelmintic activity of the stem bark extracts of Berlinia grandiflora and one of its active principles, betulinic acid. Phytomedicine. 8(2): 112-114.
Firman K, et al. (1988) Terpenoids from Curcuma heyneana. Phytochemistry. 27(12): 3887-3891.
Fleet CH, et al (1991). Cell walls. The Yeasts. 4(2): 199-277.
Furia TE, et al. (1971) Fenaroli's Handbook of Flavor Ingredients. vol. 2. 2nd Ed. CRC Press. Boca Raton.
Furia TE. (1968) Handbook of Food Additives. vol. 1. 2nd Ed. CRC Press. Boca Raton.
Gundersen DE, et al. (1996) Ultrasensitive detection of phytoplasmas by nested-PCR assays using two universal primer pairs. Phytopathologia Mediterranea. 35(3): 144-151.
Gunderson DE, et al. (1996) Genomic Diversity and Differentiation Among Phytoplasma Strains in 16S rRNA Groups I (Aster Yellows and Related Phytoplasmas) Anthill (X-Disease and Related Phytoplasmas). Int. J. Syst. Evol. Microbiol. 46(1): 64-75.
Hooser SB, et al. (1986). Effects of an insecticidal dip containing d-limonene in the cat. J Am Vet Med Assoc. 189(8): 905-908.
Ishii E, et al. (1993). Antibacterial activity of teprenone, a non water-soluble antiulcer agent, against helicobacter pylori. Int J Med Microbiol virol Parasitol Infect Dis. 280(1-2): 239-243.
Jacobs MB. (1947) Synthetic Food Adjuncts: Synthetic Food Colors, Flavors Essences, Sweetening Agents, Preservatives, Stabilizers, Viatmins and Similar Food Adjuvants. D. Van Nostrand Company, Inc.
Kadota S, et al. (1997). Antibacterial activity of trichorabdal A from Rabdosia trichocarpa against Helicobacter pylori. Zentralblatt fur Bakteriologie. 286(1): 63-67.
Karlson J, et al. (1996) Inhibition of tumor cell growth by monoterpenes in vitro: evidence of a Rasindependent mechanism of action. Anticancer Drugs. 7(4): 422- 429.

(56) References Cited

OTHER PUBLICATIONS

Khoshkhoo N, et al. (1993) Effects of bioregulators on the terpenoid aldehydes in root-knot nematode infected cotton plants. J. Agric. Food Chem. 41(12): 2442-2446.

Khoshkhoo N, et al. (1994) Terpenoid aldehydes in root-knot nematode susceptible and resistant cotton plants. J. Agric. Food Chem. 42(1) 204-208.

Khoshkhoo N, et al. (1994). Terpenoid aldehydes in root-knot nematode susceptible and resistant seeds as determined by HPLC and aniline methods. J. Agric. Food Chem. 42(3): 804-806.

Kim J, et al., (1995). Antibacterial Activity of Some Essential Oil Components against Five Foodborne Pathogens. J Agric Food Chem. 43(11): 2839-2845.

Kirkpatrick BC, et al. (1995). Phytoplasmas: can phylogeny provide the means to understand pathogenicity? Adv. Bot. Res. 21: 187-212.

Kirkpatrick BC. (1989) Strategies for characterizing plant pathogenic mycoplasma-like organisms and their effects on plants. Plant-microbe interactions (USA) (1989). pp. 241-293.

Kokalis-Burelle N, et al. (1999) Organic amendments and natural chemicals as components of transplant mixes control of root-knot nematode. Phytopathology. 89(6): S41.

Kokalis-Burelle N, et al. (2002) Development of multi-component transplant mixes for suppression of Meloidogyne incognita on tomato (*Lycopersicon esculentum*). J Nematol. 34(4): 362-369.

Kunkel LO. (1941) Heat cure of aster yellows in periwinkles. Amer J Botany. 761-769.

Ladd Jr. TL, et al. (1974) Attraction of Bumble Bees and Honey Bees to Traps Baited with Lures for the Japanese Beetle 1 2 4. J Econ Entomol. 67(2): 307-308.

Ladd TL. (1980) Japanese beetle: enhancement of lures by eugenol and caproic acid. J. Economic Entomology. 73(5): 718-720.

Lee IM, et al. (1991) Genetic Interrelatedness Among Clover Proliferation Mycoplasmalike Organisms (MIOs) and Other MIOs Investigated by Nucleic Acid Hybridization And Restriction Fragment Length Polymorphism Analyse. Appl. Environ. Micro. 57(A6112): 3565-3569.

Lee IM, et al. (1993) Universal Amplification and Analysis of Pathogen 16s rDNA for Classification and Identification of Mycoplasma-like Organisms. Phytopathology. 83: 834-842.

Lee IM, et al. (1998). Revised classification scheme of phytoplasmas based on RFLP analyses of 16S rRNA and ribosomal protein gene sequences. Intl J Systematic and Evolutionary Microbiology. 48(4): 1153-1169.

Lee PE, et al. (1963) Infectivity of Aster-Yellows Virus Preparations after Differential Cnetrifugations of Extracts from Viruliferous Leafhoppers. Virology. 21: 667-669.

Lesaffre Yeast Corporation (2013) Technical Data Sheet for Red Star Active Dry Yeast. (6 pages).

Lesaffre Yeast Corporation. (2015) Experimental Report No. 2015-00253 titled "441 Downstream Process" and dated Nov. 13, 2015. (7 pages).

Lesaffre Yeast Corporation. (2015) Experimental Report No. 2015-00305 titled "441 Downstream Process" and dated Dec. 23, 2015. (4 pages).

Mahajan R, et al. (1986). Nematicidal activity of some sesquiterpenoids against rootknot nematode (Meloidogyne incognita). Nematologica. 32(1): 119-123.

Mangel MS, et al. (1987) Nematicidal efficacy of some monoterpenes and related derivatives. Pesticides. 11(5):30-32.

Markham PG. (1982). The 'Yellows' Plant Diseases: Plant Hosts and their Interaction with the Pathogens. Plant and insect mycoplasma techniques. Springer Netherlands. pp. 82-100.

McCoy RE, et al. (1982). Chemical treatment for control of plant mycoplasma diseases. Plant and insect mycoplasma techniques. Springer Netherlands. pp. 152-172.

McCoy RE, et al. (1989) Plant diseases associated with mycoplasma-like organisms. The Mycoplasmas. 5(16): 545-640.

Mikhlin ED, et al. (1983). [Antifungal and antimicrobial activity of beta-ionone and vitamin A derivatives]. Prikl Biokhim Mikrobiol. 19(6): 795-803.

Milman IA. (1990) Alanto- and isoalantolactones. Chem. Nat. Compd. 26(3): 251-262.

Moleyar V, et al. (1992) Antibacterial activity of essential oil components. Int J Food Microbiol. 16(4): 337-342.

Momin RA, et al. (2000) Bioactive compounds and 1,3-Di[(cis)-9-octadecenoyl]-2-[(cis,cis)-9, 12-octadecadienoyl]glycerol from Apium graveolens L. seeds. J Agric Food Chem. 48(9): 3785-3788.

Mueller-Riebau F, et al. (1995) Chemical Composition and Fungitoxic Properties to Phytopathogenic Fungi of Essential Oils of Selected Aromatic Plants Growing Wild in Turkey. J. Agric. Food Chem. 43(8): 2262-2266.

Nandi B. (1977). Effect of some volatile aldehydes, ketones, esters and terpenoids on growth and development of fungi associated with wheat grains in the field and in storage. J Plant Dis Prot. 84(2): 114-128.

Nelson G, et al. (1998) Yeast delivery system. Food Ingredients and Analsysis International. September, pp. 13-14.

Oka Y, et al. (2000) Nematicidal activity of essential oils and their components against the root-knot nematode. Phytopathology. 90(7): 710-715.

Onawunmi GO. (1989) Evaluation of the antimicrobial activity of citral. Lett Appl Microbiol. 9(3): 105-108.

Pattnaik S, et al. (1997). Antibacterial and antifungal activity of aromatic constituents of essential oils. Microbios. 89(358): 39-46.

Rattray JB. (1975) Lipids of yeasts. Bacteriol Rev. 39(3):197-231.

Razin S, et al. (1998). Molecular biology and pathogenicity of mycoplasmas. Micro. Mol. Bio. Rev. 62(4): 1094-1156.

Reuveni M. (2001) Activity of trifloxystrobin against powdery and downey mildew diseases of grapevines. Can. J. Plant Pathol. 23(1): 52-59.

Rodriguez-Kabana, R. (2002). Soil fumigation: New uses for old chemicals and new compounds. Nematology 4(2):156.

Salt SD, et al. (1986) Effects of β-ionone and abscisic acid on the growth of tobacco and resistance to blue mold. Mimicry of effects of stem infection by Peronospora tabacina Adam. Physiol Mol Plant Pathol. 28(2): 287-297.

Sances FV, et al. (1992) Minimization of pesticide residues on head lettuce: Within-head residue distribution of selected insecticides. J. Econ. Etymol. 85(1): 202-207.

Sangwan NK, et al. (1985). Nematicidal activity of essential oils of Cymbopogon grasses. Nematologica. 31(1): 93-99.

Schaff D, al. (1992). Sensitive Detection and Identification of Mycoplasma-Like Organisms in Plants by Polymerase Chain Reactions. Biochem Biophys. Res. Comm. 186(3): 1503-1509.

Schmidt JO. (1994) Attraction of reproductive honey bee swarms to artificial nests by Nasonov pheromone. J. Chem. Ecol. 20(5): 1053-1056.

Shahidi F, et al. (2002) Chapter 5. Extraction and Analysis of Lipids. Food Lipids—Chemistry, Nutrition, and Biotechnology. (Eds. Akho CC and Min DB). Marcel Dekker, Inc. New York.

Siddique ABM, et al. (1998). Histopathology and Within-Plant Distribution of the Phytoplasma Associated with Australian Papaya Dieback. Plant Dis. 82(10): 1112-1120.

Sinclair WA, et al. (1989). Sampling and Histological Procedures for Diagnosis of Ash Yellows. Plant Dis. 73(5): 432-435.

Soler-Serratosa A, et al. (1996). Allelochemicals for control of plant-parasitic nematodes. 1. In vivo nematicidal efficacy of thymol and thymol/benzaldehyde combinations. Nematropica. 26(1): 57-71.

Stamp WT. (1997). Factors regulating exit of Bursaphelenchus xylophilus (Nematoda: Aphelenchoididae) fourth stage dispersal juveniles from their beetle vector Monochamus carolinensis (Coleoptera: Cerambycidae). 5452-5452.

Tominaga Y, et al. (1984). Behavioral responses of the pine wood nematode to terpenes. Agric. Biol. Chem. 48(2): 519-520.

Toner M. (Apr. 23, 2002) Report: Farms Raising Germ Resistance, Atlanta Journal Constitution (AJC). A-7.

Tsao R, et al. (2000). Antifungal Activity of Monoterpenoids against Postharvest Pathogens Botrytis cinerea and Monilinia fructicola. J. Essent. Oil Res. 12(1): 113-121.

Vasudevan P, et al. (1997). Tagetes: a multipurpose plant. Bioresour. Technol. 62(1-2): 29-35.

Veech JA. (1979). Histochemical localization and nematoxicity of terpenoid aldehydes in cotton. J Nematol. 11(3): 240.

(56) References Cited

OTHER PUBLICATIONS

Vera R. (1993). Chemical composition of the essential oil of *Ageratum conyzoides* L. (Asteraceae) from Reunion. Flavour Fragr J. 8(5): 257-260.

Wang ZM, et al. (1991). Ent-kaurene diterpenoids, isodopharicins A, B and C in Isodon pharicus. Phytochemistry. 30(11):3699-3702.

Watanabe I, et al. (1999). Nematocidal activity of picrodendrins against a species of Diplogastridae. Biol Pharm Bull. 22(12): 1310-1313.

Willett JD. (1980). Control mechanisms in nematodes. Nematodes as Biological Models.197-225.

Wuyts N, et al. (2002). Potential of plant secondary metabolites to increase resistance against plant-parasitic nematodes. Med. Fac. Landouww. Univ. Gent. 67(4): 101-104.

Xu G, et al. (1994). Study on the terpenoids in Pinus thunbergii Pad. infected with Bursaphelenchus xylophilus. Chemistry and Industry of Forest Products. 14(3): 49-54.

Xu Y, et al. (1989). Abietane quinones from Rabdosia lophanthoides. Phytochemistry. 28(1): 189-191.

Yokota M, et al. (1994) Antimicrobial effect of aromatic naturnal compound, chiefly against *Staphylcoccus aureus*. Med. Biol. Med. Biol. 128: 105-110.

Yu SG, et al. (1995). The efficacy of B-ionone in the chemoprevention of rat mammary carcinogenesis. J Agric Food Chem 43(8): 2144-2147.

Zhao JN, et al. (2000). Studies on Monochamus alternatus attractants and the attractability. Forest Research, Beijing. 13(3): 262-267.

Zhao Z, et al. (1999). Study on variations of neutral terpenoids of resistant provenances of P. massoniana after inoculating Bursaphelenchus xylophilus. Proceedings of International Symposium. Shokado Shoten, Kyoto. 217-221.

Zhao Z, et al. (2001). Study on chemical components and resistance mechanism to pine wood nematode of Masson pine provenance (II):—study on the components of neutral terpenoids and their differences among different resistant provenances of Pinus massoniana. Chemistry and Industry of Forest Products. 21(1): 56-60.

Zhao Z, et al. (2001). Study on chemical components and resistance mechanism to pine wood nematode of Masson pine provenance (III)—Study on contents variation of neutral terpenoids of resistant provenance massoniana after inoculating Bursaphelenchus xylophilus. Chemistry and Industry of Forest Products. 21(3): 52-58.

Zinovieva SV, et al. (1990). Involvement of plant sterols in the system tomatoes—nematode Meloidogyne incognita. Helminthologia 27(3): 211-216.

\* cited by examiner

PRESERVATIVES

CROSS-REFERENCE TO RELATED APPLICATIONS

This application is a national phase application of International Application No. PCT/GB2013/053065 filed Nov. 21, 2013, which claims priority to GB Application No. 1220940.9 filed Nov. 21, 2012, each of which is incorporated in its entirety by reference herein.

FIELD OF THE INVENTION

The present invention relates to a novel compositions, to methods of their preparation and to uses related thereto.

More particularly the invention relates to compositions comprising microscopic delivery systems, i.e. system for the delivery of active agents, such as pharmaceutically active agents, pesticides, such as, fungicides, bactericides, etc.

BACKGROUND TO THE INVENTION

The use of microscopic active agent delivery systems such as those comprising microcapsules, microparticles and liposomes is known.

For example, International Patent application No. WO 2006/007372 describes a particulate delivery system comprising an extracted yeast cell wall comprising beta-glucan, a payload molecule and a payload trapping molecule.

In addition, International Patent application No. WO 2005/113128 describes compositions comprising a hollow glucan particles or hollow cell wall particles encapsulating an effective amount of a terpene component which are suitable for preventing and treating infections in plants and animals, including humans, said compositions comprising 1 to 99% by volume terpenes.

Furthermore, it is known to include preservatives in such compositions, for example methyl hydroxybenzoate, ascorbic acid and sorbic acid.

Anti-mycotic materials are often added to foods to extend the usable life span of the foods to inhibit the growth of moulds, yeasts, fungi, etc.

Certain microparticle compositions comprise perishable materials, such as yeast or glucan particles. Such compositions are susceptible to degradation or spoilage by mould, yeast, or fungal growth. The usable life span of the microparticles can be drastically reduced due to spoilage by mould, yeast, or fungal growth.

It has now been surprisingly found that the inclusion in a microparticle composition of an amount of one or more terpenes, below the conventionally understood effective level, may provide a useful preservative effect on the microparticle.

SUMMARY OF THE INVENTION

Therefore, according to a first aspect of the present invention there is provided a composition comprising a microparticle component; optionally an encapsulated active agent; and a preservative amount of one or more terpenes.

Preferably the composition of this aspect of the invention includes an active agent encapsulated in the microparticle component.

A preservative amount of one or more terpenes will generally be an anti-mycotic amount, but will comprise an amount below that which is conventionally understood to be an effective amount of a terpene. The conventionally understood effective amount of a terpene, shall incorporate the use of a terpene as a therapeutically active agent, a pesticide, e.g. insecticide, fungicide, acaricide, etc.

Therefore, the term "preservative amount" or "anti-mycotic amount" of one or more terpenes shall be interpreted as meaning an anti-mycotic or antibacterial amount, i.e. an amount which is sufficient to inhibit or prevent the growth of undesirable moulds, yeasts, and/or fungi in the microparticle or in the microparticle compositions, but not sufficient to be otherwise efficacious, e.g. to environment external to the microparticles. Thus, an amount of a terpene component which may be considered to be a preservative amount or an anti-mycotic amount is 1% w/w or less, i.e. ≤1% w/w, ≤1% w/w, ≤0.9% w/w, ≤0.8% w/w, ≤0.7% w/w, ≤0.6% w/w, ≤0.5% w/w, ≤0.4% w/w, ≤0.3% w/w, ≤0.2% w/w, ≤0.1% w/w, ≤0.09% w/w, ≤0.08% w/w, ≤0.07% w/w, ≤0.06% w/w, ≤0.05% w/w, ≤0.04% w/w, ≤0.03% w/w, ≤0.02% w/w, ≤0.01% w/w of the composition. The preservative amount or anti-mycotic amount of the one or more terpenes may be from about 0.01% w/w to about 0.99% w/w.

The choice of terpene may vary and mixtures of terpenes in an appropriate amount may be used. Thus, in one embodiment the terpene component includes one or more terpenes which contain oxygen. Citral, for example citral 95, is an oxygenated $C_{10}H_{16}$ terpene, $C_{10}H_{16}O$ CAS No. 5392-40-5 (3,7-dimethyl-2,6-octadien-1-al). A stable suspension of citral can be formed up to about 2500 ppm. Citral can be made into a solution at up to about 500 ppm. A stable suspension of hollow glucan particles incorporating citral of 25 ppt citral can be made.

The one or more terpenes employed in a preservative amount or anti-mycotic amount of the composition of the present invention as hereinbefore described may comprise those which are naturally occurring and generally unmodified. Thus, the preferred terpenes are classified as GRAS (Generally Regarded as Safe) by the Environmental Protection Agency in the USA and have been used for many years in the flavour and fragrance industries. The terpenes which are exempted from US regulations and which are listed in EPA regulation 40 C.F.R. Part 152 (incorporated herein by reference in its entirety) are suitable for use in this invention. The building block of the terpenes is the 16 hydrocarbon isoprene $(C_5H_8)_n$.

The term "terpene" as used herein refers not only to terpenes of formula $(C_5H_8)_n$, but also encompasses terpene derivatives, such as terpene aldehydes or terpene polymers. Natural and synthetic terpenes are included, for example monoterpenes, sesquiterpenes, diterpenes, triterpenes, and tetraterpenes. In addition, reference to a single name of a compound will encompass the various isomers of that compound. For example, the term citral includes the cis-isomer citral-a (or geranial) and the trans-isomer. citral-b (or neral). Particularly suitable terpenes for use in the present invention include those selected from the group consisting of citral, pinene, nerol, b-ionone, geraniol, carvacrol, eugenol, carvone (for example L-carvone), terpeniol, anethole, camphor, menthol, thymol, limonene, nerolidol, farnesol, phytol, carotene (vitamin $A_1$), squalene, thymol, tocotrienol, perillyl alcohol, borneol, myrcene, simene, carene, terpenene, linalool and mixtures thereof.

The terpenes used in the present invention may have the general structure $C_{10}H_{16}$.

The terpene component may comprise a terpene selected from the group consisting of one or more of geraniol, thymol, citral, carvone (for example L-carvone), eugenol and b-ionone, or a mixture thereof. Thus, the terpene component may comprise geraniol. Alternatively, the terpene component may comprise thymol. Alternatively, the terpene component may comprise citral. Alternatively, the terpene component may comprise carvone (for example L-carvone). Alternatively, the terpene component may comprise eugenol. Alternatively, the terpene component may comprise b-ionone.

It should be noted that terpenes are also known by the names of the extract or essential oil which contain them, e. g. lemongrass oil (contains citral).

The terpene component of the present invention can comprise a single terpene or a mixture of terpenes as hereinbefore defined. One suitable terpene is citral. Another suitable terpene is a combination of terpenes. A combination of one or more of geraniol, thymol and eugenol may also be suitable, e.g. geraniol and thymol; or geraniol and eugenol; or thymol and eugenol; or geraniol, thymol and eugenol. When a combination of terpenes is used the ration of the terpenes may vary.

Certain terpene formulations which may be suitable include (percentages are w/w):
100% thymol;
100% geraniol;
100% eugenol;
100% citral; and
100% L-carvone.

Other terpene formulations which may be suitable include (percentages are w/w):
100% thymol;
50% geraniol and 50% thymol;
50% eugenol and 50% thymol;
33% geraniol, 33% eugenol and 33% thymol;
33% eugenol, 33% thymol and 33% citral;
25% geraniol, 25% eugenol, 25% thymol and 25% citral; and
20% geraniol, 20% eugenol, 20% citral, 20% thymol and 20% L-carvone.

Accordingly a terpene component comprising any of the above formulations is particularly suitable for use in the present invention.

In another embodiment the terpene component includes one or more terpenes which contain oxygen. Citral, for example citral 95, is an oxygenated $C_{10}H_{16}$ terpene, $C_{10}H_{16}O$ CAS No. 5392-40-5 (3,7-dimethyl-2,6-octadien-1-al). A stable suspension of citral can be formed up to about 2500 ppm. Citral can be made into a solution at up to about 500 ppm. A stable suspension of hollow glucan particles incorporating citral of 25 ppt citral can be made.

The terpene preservative component may comprise a terpene selected from the non-limiting group consisting of geraniol, thymol, citral, carvone (for example L-carvone), eugenol and b-ionone. The terpene preservative component can suitably comprise thymol.

Another particularly suitable terpene is citral which has demonstrated particular efficacy as a preservative.

A combination of geraniol, thymol and eugenol has demonstrated particular efficacy.

Most preferably, the terpene preservative component comprises a terpene selected from the group comprising one of more of geraniol, eugenol, carvone, citral and thymol. Thus, the terpene preservative component may comprise geraniol. The terpene preservative component may comprise eugenol. The terpene preservative component may comprise carvone. The terpene preservative component may comprise citral. The terpene preservative component may comprise thymol.

Accordingly, a composition comprising a terpene preservative component including any of the above formulations is particularly suitable for use in the present invention.

In one embodiment the terpene component includes one or more terpenes which contain oxygen. Citral, for example citral 95, is an oxygenated $C_{10}H_{16}$ terpene, $C_{10}H_{16}O$ CAS No. 5392-40-5 (3,7-dimethyl-2,6-octadien-1-al). A stable suspension of citral can be formed up to about 2500 ppm. Citral can be made into a solution at up to about 500 ppm. A stable suspension of hollow glucan particles incorporating citral of 25 ppt citral can be made.

Optionally the composition can comprise other preservative agents or anti-mycotic agents, in addition to the terpenes mentioned herein, for example known preservatives including methyl, ethyl, or n-propyl-para-hydroxybenzoates, ascorbic acid, sorbic acid, and the like.

The microparticles of the present invention may comprise a variety of such particles, including, but not limited to, microcapsules, microspheres, liposomes, yeast cell particles, glucan particles, and the like, and mixtures thereof.

Microparticles may comprise microcapsules and/or microspheres, usually consisting of substantially spherical particles, for example, 2 mm or less in diameter, usually 500 µm or less in diameter. If the particles are less than 1 µm in diameter they are often referred to as nanocapsules or nanospheres. Microcapsules and microspheres can generally be distinguished from each other by whether an active agent is formed into a central core surrounded by an encapsulating structure of a matrix material (microcapsules) or whether an active agent is dispersed throughout the matrix material particle (microspheres). It should be understood that it is within the scope of the present invention to include active agents which are encapsulated within the structure of a matrix material and active agents which are dispersed throughout a matrix material.

A description of methods of making and using microspheres and microcapsules can be found, for example, in International Patent application No. WO 09/013361, which is incorporated herein by reference.

The release of the active agent from a microcapsule or microsphere is often regulated by the biodegradation of the matrix material. A particularly well known type of microcapsule is liposomes, which can be considered to comprise microcapsules in which the active agent core is encompassed by a lipid membrane. Liposomes are artificial lipid vesicles consisting of lipid layers, where the active agent may be encapsulated inside an aqueous compartment of the liposome, or associated with the surface of the liposome via surface-coupling techniques. Liposomes can be prepared easily and inexpensively on a large scale and under mild conditions.

Other forms of microparticles are yeast cell wall particles or glucan particles. Such particles are readily available, biodegradable and substantially spherical. Yeast cell wall particles and glucan particles are generally about 2-4 µm in diameter. Preparation of extracted yeast cell wall particles is known in the art, and is described, for example, in International Patent application No. WO 2007/063268, which is incorporated herein by reference.

Yeast cell wall particles or glucan particles may be referred to as "whole glucan particles", often referred to as WGPs. Extracted yeast cell wall particles may be referred to as beta-glucan particles.

Such yeast cell wall particles may be in grown form, i.e. may have been harvested from its culture medium, and intact, i.e. not lysed, i.e. the microbe may be alive.

Extracted yeast cell wall particles may comprise hollow glucan particles or hollow cell wall particles. The term "hollow glucan particle" as used herein includes any hollow particle comprising glucan as a structural component. Thus, in particular, the term includes hollow yeast cell walls (in purified or crude forms) or hollow whole glucan particles. The term "cell wall particle" refers to a particle comprising the wall of a cell (in a purified or crude form), wherein glucan is not a structural component. Suitable particles include the cell walls of plant, algal, fungal or bacterial cells. Cell wall particles generally retain the shape of the cell from which they are derived, and thus, like a hollow glucan particle, provide a hollow central cavity suitable for encapsulating the terpene component. Particularly suitable hollow glucan particles or hollow cell wall particles are fungal cell walls, preferably yeast cell walls. Yeast cell walls are preparations of yeast cells that retain the three-dimensional structure of the yeast cell from which they are derived. Thus they have a hollow structure which allows a terpene component or an active agent to be encapsulated within the yeast cell walls. The terms hollow glucan particles or hollow yeast cell wall particles is intended to mean glucan microparticles or yeast cell particles wherein intracellular components have been substantially removed. The yeast walls may suitably be derived from, inter alia, Baker's yeast cells (available from Sigma Chemical Corp., St. Louis, Mo.). Yeast cell wall particles with desirable properties can also be obtained from Biorigin (Sao Paolo, Brazil) under the trade name Nutricell MOS 55. These particles are a spray dried extract of *S. cerevisiae*.

Alternative particles are those known by the trade names SAF-Mannan (SAF Agri, Minneapolis, Minn.) and Nutrex (Sensient Technologies, Milwaukee, Wis.). These are hollow glucan particles that are the insoluble waste stream from the yeast extract manufacturing process. During the production of yeast extracts the soluble components of partially autolysed yeast cells are removed and the insoluble residue is a suitable material for terpene loading. These hollow glucan particles comprise approximately 25-35% beta 1,3-glucan w/w. A key attribute of these materials are that they may contain more than 10% lipid w/w and are very effective at absorbing terpenes. In addition, as a waste stream product, they are a relatively cheap source of hollow glucan particles.

The one or more terpenes can be taken up in a preservative or anti-mycotic amount and stably encapsulated within hollow microparticles, such as hollow glucan particles or hollow yeast cell wall particles. Such particles are advantageous in that, inter alia, encapsulation of a preservative or anti-mycotic amount of terpenes into such particles can be achieved by incubation of the particles with the terpene.

The term "hollow glucan particle" as used herein includes any hollow particle comprising glucan, e.g. β-glucan, as a structural component. Thus, in particular, the term includes yeast hollow cell walls (in purified or crude forms) or hollow whole glucan particles. Glucan particles are generally 2-4 μm spherical, hollow, porous shells extracted from a yeast, such as Baker's yeast, *Saccharomyces cerevisae*. The surface of the glucan particles is composed primarily of 1,3-β-glucan and the particles. The hollow cavity of the glucan particles allows for efficient absorption and encapsulation of host molecules as active agents. The term "cell wall particles" refers to particles comprising the wall of a cell (in a purified or crude form), wherein glucan is not a structural component or not the main structural component.

The yeast cell wall particles may comprise, for example, Baker's yeast cell walls that are derived from baker's yeast cells and are composed of the insoluble biopolymers β-1,3-glucan, β-1,6-glucan, mannan and chitin. They are typically 2-4 μm in diameter microspheres with a shell wall that is only 0.2-0.3 μm thick surrounding an open cavity. This material has considerable liquid holding capacity, typically absorbing 5-25 times its weight in liquid. The shell is sufficiently porous that payloads up to 150,000 Daltons in size can pass through the outer shell and be absorbed into the hollow cavity of the spherical particle. Baker's yeast cell walls have several unique properties, including heat stability (e.g. to 121° C.), shear stability, pH stability (e.g. pH 2-12), and at high concentrations they do not build significant viscosity. In addition to its physical properties this composition contains natural and healthy dietary fibres that deliver cardiovascular and immunopotentiation health benefits.

Yeast cell walls are generally prepared from yeast cells by the extraction and purification of the insoluble particulate fraction from the soluble components of the yeast cell. The fungal cell walls can be produced from the insoluble by-product of yeast extract manufacture. Furthermore, the yeast cells can be treated with an aqueous hydroxide solution, without disrupting the yeast cell walls, which digests the protein and intracellular portion of the cell, leaving the yeast cell wall component devoid of significant protein contamination, and having substantially the unaltered cell wall structure of β(1-6) and β(1-3) linked glucans. A more detailed description of whole glucan particles, and the process of preparing them, is described by Jamas et al. in U.S. Pat. Nos. 4,810,646 and in 5,082,936 and 4,992,540. U.S. Pat. No. 6,242,594, assigned to Novogen Research Pty Ltd., describes a method of preparing yeast glucan particles by alkali extraction, acid extraction and then extraction with an organic solvent and finally drying. U.S. Pat. No. 5,401,727, assigned to AS Biotech-Mackzymal, discloses the methods of obtaining yeast glucan particles and methods of using them to promote resistance in aquatic animals and as an adjuvant for vaccinations. U.S. Pat. No. 5,607,677, assigned to Alpha-Beta Technology Inc., discloses the use of hollow whole glucan particles as a delivery package and adjuvant for the delivery of a variety of pharmaceutical agents. The teachings of the abovementioned patents are incorporated herein by reference.

Other types of yeast and fungi cells have cell walls that do not contain glucan. The cell walls of such yeast and fungi can be isolated by similar techniques to those mentioned above to obtain cell wall particles.

Additionally, the cells of many plants, algae, bacteria and other micro-organisms also comprise a cell wall. The structure and composition of the cell wall varies between microorganism, but in general it is a robust and relatively inert structure. It is possible to obtain cell wall particles derived from such cells through conventional techniques, such as those mentioned above in relation to yeast. Thus the term "cell wall particles" shall include yeast cell wall particles and cell wall particles derived from cells of plants, algae, bacteria, etc. as hereinbefore described.

The term "hollow glucan particle" as used herein includes any hollow particle comprising glucan as a structural component. Thus, in particular, the term includes yeast cell walls (in purified or crude forms) or hollow whole glucan particles. The term "cell wall particle" refers to a particle comprising the wall of a cell (in a purified or crude form), wherein glucan is not a structural component.

Suitable particles include the cell walls of plant, algal, fungal or bacterial cells. Cell wall particles generally retain the shape of the cell from which they are derived, and thus, like a hollow glucan particle, provide a hollow central cavity suitable for encapsulating the terpene component.

For this aspect of the present invention it is necessary that the hollow glucan particle or cell wall particle is able to stably encapsulate the terpene component. In general this means the hollow glucan particle or cell wall particle must be able to maintain its structure during incubation with the terpene component (generally the terpene component is at a relatively high concentration), and that terpene component must be able to migrate into the particle. Hollow glucan particles and cell wall particles are generally formed from relatively inert materials and are porous, and thus it can be assumed that, in general, hollow glucan particles and cell wall particles will be able to encapsulate a terpene component.

Cell wall particles generally retain the shape of the cell from which they are derived, and thus, like a hollow glucan particle, provide a hollow central cavity suitable for encapsulating the terpene component. Preferred cell wall particles are yeast cell wall particles, e.g. derived from *Saccharomyces cerevisae*.

For this aspect of the present invention it is necessary that the hollow glucan particle or cell wall particle is able to stably encapsulate the active agent component. In general this means that the hollow glucan particle or hollow cell wall particle must be able to maintain its structure during incubation with the active agent component (generally the active agent component is at a relatively high concentration), and that active agent component must be able to migrate into the hollow particle. Hollow glucan particles and hollow cell wall particles are generally formed from relatively inert materials and are porous, and thus it can be assumed that, in general, hollow glucan particles and hollow cell wall particles will be able to encapsulate an active agent component.

The present invention especially provides a composition as hereinbefore defined wherein the microparticle is a glucan particle or cell wall particle as hereinbefore described. Such glucan particles or cell wall particles may comprise live or intact particles. However, in an especially preferred embodiment of the invention the particles comprise hollow glucan particles or hollow yeast cell wall particles, that is, glucan particles or yeast cell particles wherein the intracellular components have been substantially removed and in which the glucan particles or yeast cell particles are dead.

Therefore, according to this aspect of the invention there is provided a composition comprising a hollow glucan particle or hollow yeast cell wall particle component encapsulating an active agent; and comprising a preservative amount of one or more terpenes.

Yeast cells generally comprise a cell envelope, which is a protective capsule, consisting of three major constituents, the cell wall, the plasma membrane and the periplasmic space. The cell envelope has a major role in controlling the osmotic and permeability properties of the cell. In *S. cerevisiae*, the cell envelope comprises about 15% of the total cell volume. In the embodiment of the present invention providing a hollow microparticle, such as, a hollow glucan particle or hollow yeast cell wall particle, comprising a preservative or anti-mycotic amount of one or more terpenes, the preservative terpene component may be encapsulated in the hollow microparticle.

Alternatively, the preservative terpene component may be held in the cell envelope. It will be understood by the person skilled in the art that it is within the scope of the present invention for a part of the preservative terpene component to be encapsulated and part to be housed in the cell wall as hereinbefore described.

Particularly suitable hollow glucan particles or cell wall particles are fungal cell walls, preferably yeast cell walls.

Yeast cell walls are preparations of yeast cells that retain the three-dimensional structure of the yeast cell from which they are derived. Thus they have a hollow structure which allows the active agent component to be encapsulated within the yeast cell walls. The yeast walls may suitably be derived from Baker's yeast cells (available from Sigma Chemical Corp., St. Louis, Mo.). Yeast cell wall particles with desirable properties can also be obtained from Biorigin (Sao Paolo, Brazil) under the trade name Nutricell MOS 55. These particles are a spray dried extract of *S. cerevisiae*.

Alternative particles are those known by the trade names SAF-Mannan (SAF Agri, Minneapolis, Minn.) and Nutrex (Sensient Technologies, Milwaukee, Wis.). These are hollow glucan particles that are the insoluble waste stream from the yeast extract manufacturing process. During the production of yeast extracts the soluble components of partially autolysed yeast cells are removed and the insoluble residue is a suitable material for active agent loading. The amount of beta 1,3-glucan in the hollow glucan particles may vary and may be from about 25 to about 90% beta 1,3-glucan w/w. SAF-Mannan hollow glucan particles comprise approximately 25-35% beta 1,3-glucan w/w. A key attribute of these materials are that they contain more than 10% lipid w/w and are very effective at absorbing active agents. In addition, as a waste stream product they are a relatively cheap source of hollow glucan particles.

Alternative hollow glucan particles which have higher purity are those produced by Nutricepts (Nutricepts Inc., Burnsville, Minn.) and ASA. Biotech. These particles have been alkali extracted, which removes additional intracellular components as well as removes the outer mannoprotein layer of the cell wall yielding a particle of 50-65% w/w glucan.

Higher purity hollow glucan particles are the WGP particles from Biopolymer Engineering. These particles are acid extracted removing additional yeast components yielding a product 75-85% w/w glucan.

Very high purity hollow glucan particles are Adjuvax® from Alpha-beta Technology, Inc. (Worcester, Mass.) and microparticulate glucan from Novogen (Stamford, Conn.). These particles are organic solvent extracted which removes residual lipids and so the particles may comprise more than 90% w/w glucan.

In some embodiments a high purity hollow glucan particle or hollow cell wall particle may be required, for example where strict control over possible contaminants is required. In these instances the higher purity particles would be preferred over other less pure products. For other embodiments, the less pure particles would be preferred for economic reasons; those particles have also been found to be more effective at absorbing certain active agents.

Preferably the hollow glucan particle or cell wall particle has a slight lipid content, such as 1 or 2% w/w lipid. A slight lipid content can increase the ability of the particle to encapsulate the terpene component. The lipid content of the hollow glucan particle or cell wall particle is 5% w/w or greater, or 10% w/w or greater.

Thus, the lipid content of the microparticles, e.g. the hollow glucan particle or hollow cell wall particle may be ≥1% w/w, or ≥2% w/w, or ≥3% w/w, or ≥4% w/w, or ≥5% w/w, or ≥6% w/w, or ≥7% w/w, or ≥8% w/w, or ≥9% w/w, or ≥10% w/w, or ≥15% w/w, or ≥20% w/w, or ≥25%. Thus, the lipid content may be from about 1% to about 25% w/w, or from about 2% to about 20% w/w, or from about 5% to about 15% w/w, e.g. about 10% w/w.

By way of example only, active agents for use in the microcapsules of the present invention include, but shall not be limited to, biologically active agents, such as pharmaceutically active agents and pesticides. Biologically active compounds may also include, for example, a plant nutritive substance or a plant growth regulant. Alternatively, the active agent may be non-biologically active, such as, a plant nutritive substance, a food flavouring, a fragrance, and the like.

Hereinafter the reference to the microparticle delivery system shall include the preserved microparticle, i.e. a microparticle including a preservative amount of a terpene component.

Pharmaceutically active agents refer to naturally occurring, synthetic, or semi-synthetic materials (e.g., compounds, fermentates, extracts, cellular structures) capable of eliciting, directly or indirectly, one or more physical, chemical, and/or biological effects, in vitro and/or in vivo. Such active agents may be capable of preventing, alleviating, treating, and/or curing abnormal and/or pathological conditions of a living body, such as by destroying a parasitic organism, or by limiting the effect of a disease or abnormality by materially altering the physiology of the host or parasite. Such active agents may be capable of maintaining, increasing, decreasing, limiting, or destroying a physiologic body function. Active agents may be capable of diagnosing a physiological condition or state by an in vitro and/or in vivo test. The active agent may be capable of controlling or protecting an environment or living body by attracting, disabling, inhibiting, killing, modifying, repelling and/or retarding an animal or microorganism. Active agents may be capable of otherwise treating (such as deodorising, protecting, adorning, grooming) a body. Depending upon the effect and/or its application, the active agent may further be referred to as a bioactive agent, a pharmaceutical agent (such as a prophylactic agent, or a therapeutic agent), a diagnostic agent, a nutritional supplement, and/or a cosmetic agent, and includes, without limitation, prodrugs, affinity molecules, synthetic organic molecules, polymers, molecules with a molecular weight of 2 kD or less (such as 1.5 kD or less, or 1 kD or less), macromolecules (such as those having a molecular weight of 2 kD or greater, preferably 5 kD or greater), proteinaceous compounds, peptides, vitamins, steroids, steroid analogues, lipids, nucleic acids, carbohydrates, precursors thereof and derivatives thereof. Active agents may be ionic, non-ionic, neutral, positively charged, negatively charged, or zwitterionic, and may be used singly or in combination of two or more thereof. Active agents may be water insoluble, or water soluble.

The term "macromolecule" used herein refers to a material capable of providing a three-dimensional (e.g., tertiary and/or quaternary) structure.

A wide variety of pharmaceutically active agents may be utilised in the present invention. Thus, the pharmaceutically active agent may comprise one or more of a polynucleotide, a peptide, a protein, a small organic active agent, a small inorganic active agent and mixtures thereof.

A polynucleotide active agent may comprise one or more of an oligonucleotide, an antisense construct, a siRNA, an enzymatic RNA, a recombinant DNA construct, an expression vector, and mixtures thereof. The microparticle delivery system of the present invention may be useful for in vivo or in vitro delivery of active agents, such as, amino acids, peptides and proteins. Peptides can be signalling molecules such as hormones, neurotransmitters or neuromodulators, and can be the active fragments of larger molecules, such as receptors, enzymes or nucleic acid binding proteins. The proteins can be enzymes, structural proteins, signalling proteins or nucleic acid binding proteins, such as transcription factors.

When the pharmaceutically active agent comprises a small organic active agent it may comprise a therapeutic agent or a diagnostic agent. In particular embodiments a small organic active agent may comprise a sequence-specific DNA binding oligomer, an oligomer of heterocyclic polyamides, for example, those disclosed in U.S. Pat. No. 6,506,906 which is hereby incorporated by reference. Other small organic active agents may comprise those disclosed in and by Dervan in "Molecular Recognition of DNA by Small Molecules, Bioorganic & Medicinal Chemistry (2001) 9: 2215-2235", which is hereby incorporated by reference. In certain embodiments, the oligomer may comprise monomeric subunits selected from the group consisting of N-methylimidazole carboxamide, N-methylpyrrole carboxamide, beta-alanine and dimethyl aminopropylamide.

In another embodiment of the present invention the microparticle delivery system of the present invention may include an inorganic active agent, e.g. gastrointestinal therapeutic agents such as aluminium hydroxide, calcium carbonate, magnesium carbonate, sodium carbonate and the like.

In another embodiment of the invention, more than one type of polynucleotide may be enclosed within the microparticle delivery system. Such polynucleotides provide the ability to express multiple gene products under control, in certain embodiments, at least one expressible gene product is a membrane protein, such as a membrane receptor, most preferably a membrane-bound receptor for a signalling molecule. In some embodiments, at least one expressible gene product is a soluble protein, such as a secreted protein, e.g. a signalling protein or peptide. In other embodiments, the present invention provides a method of delivering a drug to a macrophage cell including the steps of providing a substantially spherical extracted hollow yeast cell wall comprising beta-glucan, the hollow yeast cell wall defining an internal space; contacting the extracted hollow yeast cell wall with a pharmaceutically active agent wherein the pharmaceutically active agent is, at least partially, enclosed within the internal space to form a particulate drug delivery system; and contacting a macrophage cell with the particulate drug delivery system. The method may also include the step of internalising the microparticle drug delivery system by the macrophage. In another embodiment, the method may also include the step of transporting the drug delivery system by the macrophage. The macrophage may deliver the microparticle drug delivery system to a macrophage-attracting site, such as a site of infection, inflammatory reaction, hypoxia or hyperplasia. In certain embodiments, the macrophage may deliver the microparticle drug delivery system to a tumour. In another embodiment, the method may include the step of releasing the drug or pharmaceutically active agent from the microparticle drug delivery system, optionally further including the step of releasing the drug or pharmaceutically active agent into the extracellular space. In certain embodiments, the step of releasing the drug or pharmaceutically active agent includes the steps of expressing a recombinant protein and secreting the protein into the extracellular space.

The present invention also provides a method of immunising an individual against a pathogen. The method may comprise the step of contacting cells of said individual with a microparticle delivery system comprising a microparticle, e.g. an extracted hollow yeast cell wall comprising beta-glucan, and a nucleic acid composition, thereby administering to the cells a nucleic acid molecule that comprises a nucleotide sequence that encodes a peptide which comprises at least an epitope identical to, or substantially similar to, an epitope displayed on said pathogen as antigen, and said nucleotide sequence is operatively linked to regulatory sequences, wherein the nucleic acid molecule is capable of being expressed in the cells of the individual. In another embodiment, the present invention provides a method of producing immunity to a toxoid comprising the steps of providing a microparticle delivery system comprising a microparticle, e.g. an extracted hollow yeast cell wall comprising beta-glucan and a toxoid, contacting a phagocytic cell with the microparticle delivery system and inducing phagocytosis of the microparticle delivery system. The phagocytic cell can be one or more of macrophages, M cells of the Peyer's patches, monocytes, neutrophils, dendritic cells, Langerhans cells, Kupffer cells, alveolar phagocytes, peritoneal macrophages, milk macrophages, microglia, eosinophils, granulocytes, mesengial phagocytes, and synovial A cells.

The present invention provides a method of immunising an individual against a hyperproliferative disease or an autoimmune disease. The method may comprise the step of contacting cells of said individual with a microparticle delivery system comprising a microparticle, e.g. an extracted hollow yeast cell wall comprising beta-glucan and a nucleic acid composition, thereby administering to the cells a nucleic acid molecule that comprises a nucleotide sequence that encodes a peptide which comprises at least an epitope identical to, or substantially similar to, an epitope displayed on a hyperproliferative disease-associated protein or an autoimmune disease-associated protein, respectively, and is operatively linked to regulatory sequences, wherein the nucleic acid molecule is capable of being expressed in the cells of the individual.

The present invention also provides a method of treating an individual suffering from an autoimmune disease comprising the step of contacting cells of said individual with a microparticle delivery system comprising a microparticle e.g. an extracted hollow yeast cell wall comprising beta-glucan and a nucleic acid composition, thereby administering to the cells a nucleic acid molecule that comprises a nucleotide sequence that restores the activity of an absent, defective or inhibited gene, or that encodes a protein that produces a therapeutic effect in the individual, and is operatively linked to regulatory sequences; the nucleic acid molecule being capable of being expressed in said cells. In a further embodiment, the present invention provides a method of immunising an individual against a hyperproliferative disease comprising the step of contacting cells of said individual with a microparticle delivery system comprising a microparticle, e.g. an extracted hollow yeast cell wall comprising beta-glucan and a polynucleotide comprising a control sequence operatively linked to an open reading frame encoding a peptide that comprises an epitope identical to, or substantially similar to, an epitope displayed on a hyperproliferative disease-associated protein, wherein encoded peptide is capable of being expressed in the cells of the individual.

In another embodiment, the present invention provides a method of treating an individual suffering from a genetic disease comprising the step of contacting the cells of said individual with a microparticle delivery system comprising a microparticle, e.g. an extracted hollow yeast cell wall comprising beta-glucan, and a polynucleotide thereby administering to the cells a polynucleotide that comprises a nucleotide sequence that restores the activity of an absent, defective or inhibited gene. The polynucleotide may comprise a regulatory sequence operatively linked to an open reading frame encoding a protein that produces a therapeutic effect in the individual, the protein being capable of being expressed in said cells.

The present invention also relates to methods of treating an individual suffering from an autoimmune disease comprising the steps of contacting cells said individual with a microparticle delivery system comprising a microparticle, e.g. an extracted hollow yeast cell wall comprising beta-glucan and a nucleic acid composition, thereby administering to the cells a nucleic acid molecule that comprises a nucleotide sequence that restores the function of an absent, defective or inhibited gene, or that encodes a protein that produces a therapeutic effect in the individual, and is operatively linked to regulatory sequences; the nucleic acid molecule being capable of being expressed in said cells.

Accordingly the present invention also provides compositions and methods which prophylactically and/or therapeutically immunise an individual against a pathogen or abnormal, disease-related cell. The genetic material encodes a peptide or protein that shares at least an epitope with an immunogenic protein found on the pathogen or cells to be targeted. The genetic material is expressed by the individual's cells and serves as an immunogenic target against which an immune response is elicited. The resulting immune response is broad based: in addition to a humoral immune response, both arms of the cellular immune response are elicited. The methods of the present invention are useful for conferring prophylactic and therapeutic immunity. Thus, a method of immunising includes both methods of protecting an individual from pathogen challenge, or occurrence or proliferation of specific cells, as well as methods of treating an individual suffering from pathogen infection, hyperproliferative disease or autoimmune disease. Thus, the present invention is useful to elicit broad immune responses against a target protein, i.e. proteins specifically associated with pathogens or the individual's own "abnormal" cells. The present invention is also useful in combating hyperproliferative diseases and disorders such as cancer, by eliciting an immune response against a target protein that is specifically associated with the hyperproliferative cells. Such cancers include, but shall not be limited to are selected from one or more of primary cancer, breast cancer, colon cancer, prostate cancer, non-small cell lung cancer, glioblastoma, lymphoma, mesothelioma, liver cancer, intrahepatic bile duct cancer, oesophageal cancer, pancreatic cancer, stomach cancer, laryngeal cancer, brain cancer, ovarian cancer, testicular cancer, cervical cancer, oral cancer, pharyngeal cancer, renal cancer, thyroid cancer, uterine cancer, urinary bladder cancer, hepatocellular carcinoma, thyroid carcinoma, osteosarcoma, small cell lung cancer, leukaemia, myeloma, gastric carcinoma and metastatic cancers.

The present invention is further useful in combating autoimmune diseases and disorders by eliciting an immune response against a target protein that is specifically associated with cells involved in the autoimmune condition.

The present invention also provides a pharmaceutical kit that comprises a container comprising a pharmaceutically active agent selected from the group consisting of a nucleic acid composition, protein composition, small organic molecule and mixtures thereof, and a container comprising a microparticle, e.g. a hollow yeast cell wall particle. Optionally, such a kit may include one or more excipients, carriers, preservatives and vehicles of the type described herein with respect to pharmaceutical compositions. The term pharmaceutical kit is also intended to include multiple inoculants used in the methods of the present invention. Such kits include separate containers comprising different inoculants and transfer moieties. The pharmaceutical kits in accordance with this aspect of the present invention are also contemplated to include a set of inoculants used in the treatment and immunising methods and/or therapeutic methods, as described herein.

Non-limiting macromolecules used to form the microparticles include, inter alia, polymers, copolymers, proteins (e.g., enzymes, recombinant proteins, albumins such as human serum albumin, monoclonal antibodies, polyclonal antibodies), peptides, lipids, carbohydrates (e.g., monosaccharides, disaccharides, polysaccharides), nucleic acids, vectors (e.g., virus, viral particles), and complexes and conjugates thereof (e.g., covalent and/or non-covalent associations between two macromolecules such as carbohydrate-protein complexes or conjugates, or between an active agent and a macromolecule such as hapten-protein complexes or conjugates). Macromolecules may be neutral, positively charged, negatively charged, or zwitterionic, and may be used singly or in combination of two or more thereof.

"Proteinaceous compounds" refer to natural, synthetic, semi-synthetic, or recombinant compounds of or related structurally and/or functionally to proteins, such as those containing or consisting essentially of α-amino acids covalently associated through peptide linkages. Non-limiting proteinaceous compounds include globular proteins (e.g. albumins, globulins, histones), fibrous proteins (e.g. collagens, elastins, keratins), compound proteins (including those containing one or more non-peptide component, e.g. glycoproteins, nucleoproteins, mucoproteins, lipoproteins, metalloproteins), therapeutic proteins, fusion proteins, receptors, antigens (such as synthetic or recombinant antigens), viral surface proteins, hormones and hormone analogues, antibodies (such as monoclonal or polyclonal antibodies), enzymes, Fab fragments (fragment antigen binding), cyclic peptides, linear peptides, and the like. Non-limiting therapeutic proteins include bone morphogenic proteins, drug resistance proteins, toxoids, erythropoietins, proteins of the blood clotting cascade (e.g. Factor VII, Factor VIII, Factor IX), subtilisin, ovalbumin, alpha-1-antitrypsin (AAT), DNase, superoxide dismutase (SOD), lysozyme, ribonuclease, hyaluronidase, collagenase, human growth hormone (hGH), erythropoietin, insulin and insulin-like growth factors or their analogues, interferons, glatiramer, granulocyte-macrophage colony-stimulating factor, granulocyte colony-stimulating factor, desmopressin, leutinizing hormone release hormone (LHRH) agonists (e.g., leuprolide, goserelin, buserelin, gonadorelin, histrelin, nafarelin, deslorelin, fertirelin, triptorelin), LHER antagonists, vasopressin, cyclosporine, calcitonin, parathyroid hormone, parathyroid hormone peptides, insulin, glucogen-like peptides, and analogues thereof.

Proteinaceous compounds may be neutral, positively charged, negatively charged, or zwitterionic, and may be used singly or in combination of two or more thereof.

"Peptides" refer to natural, synthetic, or semi-synthetic compounds formed at least in part from two or more of the same or different amino acids and/or imino acids. Non-limiting examples of peptides include oligopeptides (such as those having less than 50 amino/imino acid monomer units, including dipeptides and tripeptides and the like), polypeptides, proteinaceous compounds as defined herein, as well as precursors and derivatives thereof (e.g., glycosylated, hyperglycosylated, PEGylated, FIT C-labelled, and salts thereof). Peptides may be neutral, positively charged, negatively charged, or zwitterionic, and may be used singly, or in combination of two or more thereof.

"Lipids" refer to natural, synthetic, or semi-synthetic compounds that are generally amphiphilic. The lipids typically comprise a hydrophilic component and a hydrophobic component. Non-limiting examples include fatty acids, neutral fats, phosphatides, oils, glycolipids, surfactants, aliphatic alcohols, waxes, terpenes and steroids. Lipids may be ionic, non-ionic, neutral, positively charged, negatively charged, or zwitterionic, and may be used singly or in combination of two or more thereof.

"Nucleic acids" refer to natural, synthetic, semi-synthetic, or recombinant compounds formed at least in part from two or more of the same or different nucleotides, and may be single-stranded or double-stranded. Non-limiting examples of nucleic acids include oligonucleotides (such as those having 20 or less base pairs, e.g., sense, anti-sense, or missense), aptamers, polynucleotides (e g., sense, anti-sense, or missense), DNA (e.g., sense, anti-sense, or missense), RNA (e.g., sense, anti-sense, or missense), siRNA, nucleotide acid constructs, single-stranded or double-stranded segments thereof, as well as precursors and derivatives thereof (e.g., glycosylated, hyperglycosylated, PEGylated, FITC-labelled, nucleosides, and salts thereof). Nucleic acids may be neutral, positively charged, negatively charged, or zwitterionic, and may be used singly or in combination of two or more thereof.

"Carbohydrates" refer to natural, synthetic, or semi-synthetic compounds formed at least in part from monomeric sugar units. Non-limiting carbohydrates include polysaccharides, sugars, starches, and celluloses, such as carboxymethylcellulose, dextrans, hetastarch, cyclodextrins, alginates, chitosans, chondroitins, heparins, as well as precursors and derivatives thereof (e.g., glycosylated, hyperglycosylated, PEGylated, FITC-labelled, and salts thereof). Carbohydrates may be ionic or non-ionic, may be neutral, positively charged, negatively charged, or zwitterionic, and may be used singly or in combination of two or more thereof.

Suitable pesticides include, for example, herbicides, insecticides, and fungicides. As biologically active compounds, there may specifically be mentioned insecticidal compounds, fungicidal compounds, nematicidal compounds, herbicidal compounds, etc.

When the active agent is an insecticide, suitable insecticidal agents include, but shall not be limited to, pyrethroid, pyrethrin, or a combination thereof. Optionally, the insecticide may comprise at least one pyrethroid such as allethrin, d-allethrin, d-trans allethrin, alfoxylate, bioresmethrin, cyfluthrin, beta-cyfluthrin, cyhalothrin, lambda cyhalothrin, gamma cyhalothrin, bifenthrin, cypermethrin, beta cypermethrin, zeta cypermethrin, cyphenothrin, deltamethrin, tetramethrin, esfenvalerate, fenfluthrin, fenopropathrin, fenpyrithrin, fenvalerate, fluorocythrin, furamethrin, fluvalinate, imiprothrin, permethrin, phencyclate, phenothrin, prallethrin, resmethrin, s-bioallethrin, tau-fluvalinate, tefluthrin, tetrallethrin, tralocythrin and tralomethrin or a combination thereof. Additionally, any combination of the above pesticides can be used.

When the active agent is a fungicide, suitable fungicidal agents include, but shall not be limited to, sulfenamides, such as dichlofluanid, tolylfluanid, folpet and fluorofolpet; benzimidazoles, such as carbendazim (MBC), benomyl, fuberidazole and thiabendazole and salts thereof; thiocyanates, such as thiocyanatomethyl thiobenzo-thiazole (TC-MTB) and methylene bisthiocyanate (MBT); quaternary ammonium compounds, such as benzyl dimethyltetradecylammonium chloride, benzyldimethyl dodecyl-ammonium chloride and dodecyl-dimethylammonium chloride; morpholine derivatives, such as tridemorph, fenpropimorf and falimorph; phenols, such as o-phenylphenol, tribromophenol, tetrachlorophenol, pentachlorophenol, 3-methyl-4-chlorophenol, dichlorophen and chlorophen and salts thereof; azoles, such as triadimefon, triadimenol, bitertanol, tebuconazole, propiconazole, azaconazole, hexaconazole, prochloraz, cyproconazole; iodopropargyl derivatives, such as iodopropargyl-butylcarbamate (IPBC) and iodo-propargyloxyethyl phenylcarbamate; iodo derivatives, for example diiodomethyl-p-aryl-sulfones, such as diiodomethyl-p-tolyl-sulfone; bromo derivatives, such as bromopol; isothiazolines, such as N-methylisothiazolin-3-one, octilinone, benzisothiazolinone and cyclopentene-isothiazoline; pyridines, such as 1-hydroxy-2-pyridinethione and tetrachloro-4-methylsulfonylpyridine; nitriles, such as chlorothalonil; benzothiazoles, such as 2-mercaptobenzothiazole; dicarboximides, such as iprodione, vinclozolin, procymidorie and dazomet; and quinolines, such as 8-hydroxyquinoline.

When the active agent is a herbicide, such herbicidal compounds are suitable to control the growth of undesired plants, such as shrubs and bushes. Suitable herbicidal agents include, but shall not be limited to, 2,4-D, aminopyralid, atrazine, clopyralid, dicamba, glufosinate ammonium, fluroxypyr, glyphosate, imazapyr, imazapic, imazamox, linuron, metolachlor, paraquat, pendimethalin, picloram, sodium chlorate and triclopyr.

The following compounds may be mentioned as examples of plant nutritive substances, which can be present in the capsule preparations according to the invention: Water-soluble metal compounds having a chlorophyll based structure, such as sodium chlorophyllin and sodium copper chlorophyllin; water-soluble compounds which provide an element selected from the group consisting of iron, zinc and magnesium, including, as water-soluble iron compounds, ferrous chloride, ferrous nitrate, ferrous sulphate, ammonium ferrous sulphate, ferric acetate, ferric chloride, ferric nitrate, ferric sulphate, ferric citrate, ammonium iron citrate, iron glycerophosphate, ferric tartrate, ferric lactate, ferric glycolate, etc.; water-soluble magnesium compounds and water-soluble zinc compounds which correspond to these water-soluble iron compounds; and ferric-zinc double salts, ferric-manganese double salts, or zinc-manganese double salts, etc. of citrate and sulphate.

The microparticle preparations according to the invention can contain one biologically active compound or combinations of two or more of such compounds.

The microparticle preparations according to the invention can contain the biologically active compounds as such or in admixture with one or more pharmaceutically or agriculturally acceptable auxiliaries, such as carriers, extenders, stabilisers, surface-active agents and colorants.

In a particular aspect of the present invention there is provided a microparticle delivery system comprising a microparticle, an encapsulated active agent and a preservative amount of a terpene component. According to this aspect of the invention the microparticle may comprise yeast cell particles or glucan particles, preferably hollow yeast cell particles or hollow glucan particles.

In another aspect of the invention, when a solvent system is required, the solvent system may comprise water.

The microparticle delivery system of this aspect of the present invention may be useful for, inter alia, both in vivo and in vitro delivery of active agents. Therefore, the compositions and/or the microparticle delivery system of the invention may be useful in the fields of human and/or veterinary medicine and/or agricultural welfare, including, without limitation, the treatment of mammals, e.g. including human, bovine, ovine, porcine, equine, canine and feline species; birds, fish, arthropods and/or plants.

In certain embodiments extracted yeast cell walls comprise less than 90 weight percent beta-glucan. In certain embodiments the extracted yeast cell walls comprises more than 50 weight percent chitin. In another embodiment the extracted yeast cell walls further comprise more than 30 weight percent mannan. In other certain embodiments the extracted yeast cell wall includes more than 1 weight percent protein. For the avoidance of doubt, extracted yeast cell walls shall be considered to be yeast cells that have had their intracellular components removed, i.e. hollow yeast cells.

The microparticle compositions according to the present invention can contain one or more biologically active agents or combinations of two or more of such agents.

The microparticle compositions according to the invention can contain the biologically active compounds as such or in admixture with one or more pharmaceutically or agriculturally acceptable auxiliaries, such as carriers, extenders, stabilisers, surface-active agents and colorants.

The amount of active agent in the composition may vary, depending upon, inter alia, the nature of the active agent, the intended use of the composition, etc.

Thus, the composition of the present invention can comprise from about 1 ppm to about 25 ppt (25,000 ppm) of the active agent component, based on the total composition, preferably from about 10 to about 5,000 ppm of the active agent component, from about 10 to about 5,000 ppm, from about 100 to about 4,000 ppm, from about 200 to about 3,000 ppm, from about 300 to about 2,000 ppm, from about 400 to about 1,500 ppm, from about 500 to about 1,000 ppm. For example, 250, 500, 1000, 2000 ppm thereof. Alternatively, the amount of the active agent component in the composition of the present invention may comprise from about 0.1% w/w to about 90% w/w of the composition, based on the total composition. Therefore, the amount of the active agent in the composition may be from about 1% w/w to about 90% w/w, from about 2% w/w to about 90% w/w, from about 3% w/w to about 90% w/w, from about 4% w/w to about 90% w/w, from about 5% w/w to about 90% w/w, from about 6% w/w to about 90% w/w, from about 7% w/w to about 90% w/w, from about 8% w/w to about 90% w/w, from about 9% w/w to about 90% w/w, from about 10% w/w to about 90% w/w, from about 15% w/w to about 90% w/w, from about 20% w/w to about 90% w/w, from about 25% w/w to about 90% w/w, from about 30% w/w to about 90% w/w, from about 35% w/w to about 90% w/w, from about 40% w/w to about 90% w/w, from about 45% w/w to about 90% w/w, from about 50% w/w to about 90% w/w, from about 60% w/w to about 90% w/w, from about 70% w/w to about 90% w/w, from about 80% w/w to about 90% w/w, of the composition.

Optionally the terpene component and/or the biologically active agent component of the composition of the present invention can be associated with a surfactant. The surfactant can be non-ionic, cationic, or anionic.

Examples of suitable surfactants include sodium lauryl sulphate, polysorbate 20, polysorbate 80, polysorbate 40, polysorbate 60 polyglyceryl ester, polyglyceryl monooleate, decaglyceryl monocaprylate, propylene glycol dicaprilate, triglycerol monostearate, polyoxyethylenesorbitan, monooleate, Tween®, Span® 20, Span® 40, Span® 60, Span® 80, Brig 30 or mixtures thereof. The surfactant acts to hold the terpene component and/or the biologically active component in an emulsion and also assists encapsulation of the terpene component into the microparticle, e.g. hollow glucan particle or hollow cell wall particle.

The encapsulated active agent component of the composition of the invention, i.e. the microparticle/biologically active agent component of the composition, can comprise 1 to 99% w/w active agent and 1 to 99% w/w microparticle, e.g. hollow glucan particles or hollow cell wall particles. More specifically the composition can comprise about 10% w/w microparticle and about 90% w/w active agent, about 15% w/w microparticle and about 85% w/w active agent, about 20% w/w microparticle and about 80% w/w active agent, about 25% w/w microparticle and about 75% w/w active agent, about 30% w/w microparticle and about 70% w/w active agent, about 35% w/w microparticle and about 65% w/w active agent, about 40% w/w microparticle and about 60% w/w active agent, about 45% w/w microparticle and about 55% w/w active agent, e.g. about 50% w/w microparticle and about 50% w/w active agent. The composition may optionally comprise from about 0.1 to about 10% w/w surfactant.

Suitably a composition of the present invention comprises from about 500 to about 10,000 ppm microparticles, e.g. hollow glucan particles or hollow cell wall particles, where the particles contain a preservative amount of one or more terpenes as hereinbefore described. Preferably the composition comprises from about 1,000 to about 2,000 ppm microparticles, e.g. hollow glucan particles or hollow cell wall particles, where the particles contain a preservative amount of one or more terpenes and from about 0.1% w/w to about 90% w/w of an active agent component.

Concentrations of hollow glucan particles or hollow cell wall particles in the composition of the invention, for encapsulation of an active agent, of about 1, 5, 10, 20, 30, 40, 50, 60, 70, 80, 90, 100, 110, 125, 130, 140, 150, 160, 175, 190, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1250, 1375, 1425, 1500, 1600, 1750, or 2000 ppm can be used as effective concentrations in the compositions and methods of the current invention. Even higher concentrations (up to 25 ppt, i.e. parts per thousand) can be made and may be useful in the current invention.

Optionally the composition can comprise other active compounds in addition to those specifically mentioned herein, for example other antimicrobial agents, enzymes, and the like.

The compositions of the invention may also comprise an antioxidant component to reduce oxidation of the microcapsule and/or the active agents. An example of such an anti-oxidant might be rosemary oil, vitamin C or vitamin E.

The compositions of the present invention may be in the form of a dry powder. The compositions may be provided in combination with an agriculturally, food or pharmaceutically acceptable carrier or excipient in a liquid, solid or gel-like form.

For solid compositions, suitable carriers include pharmaceutical or agricultural grades of mannitol, lactose, starch, magnesium stearate, sodium saccharin, talc, cellulose, glucose, sucrose, magnesium carbonate, and the like. Suitably the composition may be formulated in tablet or pellet form.

A pellet, tablet or other solid form of the composition can preferably also contain a dispersal agent which promotes dispersal of the composition when placed into a liquid, e.g. water. Suitable dispersal agents include xanthan gum, maltodextrin, alginates, or the like.

Liquid compositions can, for example, be prepared by dispersing the composition in water, saline, aqueous dextrose, glycerol, ethanol, or the like, to form a solution or suspension. If desired, these compositions can contain minor amounts of non-toxic auxiliary substances such as wetting or emulsifying agents, pH buffering agents (for example, sodium acetate, sorbitan monolaurate, triethanolamine sodium acetate or triethanolamine oleate). The methods of preparing such liquid compositions are known, or will be apparent, to those skilled in this art. A liquid composition could be prepared by dispersing the composition in a liquid food or drink material. Additionally a suitable liquid pharmaceutically acceptable or agriculturally acceptable excipient could be used.

Conventionally known carriers, aqueous, powder or oily bases, thickeners, and the like can be used as necessary or desirable.

The present invention further provides a method of delivering an active agent to a recipient, comprising the steps of:
  providing a microparticle component including a preservative amount of one or more terpenes;
  (ii) contacting the microparticle with the active agent wherein the active agent becomes, at least partially, encapsulated within the microparticle;
  (iii) contacting the recipient with the active agent encapsulating microparticle component.

The recipient may comprise one or more cells or mammals, e.g. including human, bovine, ovine, porcine, equine, canine and feline species; birds, fish, arthropods and/or plants.

The invention further provides a method of treating a body with an active agent comprising the step of contacting the cells of the individual with a composition comprising a microparticle component, including a preservative amount of one or more terpenes, and an active agent, thereby administering to the cells in an effective amount of the active agent.

In the method of treatment of this aspect of the invention, where the active agent is a pharmaceutically active agent, the body may comprise a mammal e.g. bovine, ovine, porcine, equine, canine and feline species. The mammal may especially comprise a human.

Where the active agent is a pharmaceutically active agent, the invention may further provide a method of treating a patient suffering from a disorder, said method comprising administering an affective amount of an active agent in the form of a composition comprising an active agent encapsulated in a microparticle component; said microparticle component comprising a preservative amount of one or more terpenes.

Where the active agent is a pesticide, e.g. an insecticide, the invention may further provide a method of killing a pest, e.g. an arthropod, said method comprising administering an affective amount of an active agent in the form of a composition comprising an active agent encapsulated in a microparticle component; said microparticle component comprising a preservative amount of one or more terpenes.

The method according to this aspect of the invention may comprise administering the pesticide to a body, plant, etc. Where the active agent is a pesticide, e.g. an insecticide, the invention may further provide a method of killing a pest, e.g. an arthropod, said method comprising administering an affective amount of an active agent in the form of a composition comprising an active agent encapsulated in a microparticle component; said microparticle component comprising a preservative amount of one or more terpenes.

It will be understood by the person skilled in the art that this method of the invention may comprise applying the composition of the invention directly to a body as hereinbefore described, or to a plant or to a pest.

The term pesticide may include fungicide, insecticide, acaricide, bactericide, herbicide, rodenticide, etc.

According to this aspect of the invention the term "arthropods" includes insects and arachnids, such as, but not limited to, ticks, mites, fleas, mosquitoes, midges, etc.

The amount of composition administered will, of course, be dependent on the manner of administration, on the targeted, etc. Suitable compositions are those defined in more detail above.

The amount of active agent administered in the above method should clearly be sufficient to achieve the desired result, i.e. to be fatal to the pest, e.g. arthropod, such as an insect or arachnid, fungus, bacteria, etc., but should not be at a level which will induce serious toxic effects in mammals, especially humans.

Incorporation of an active agent component in a microparticle, e.g. a hollow glucan particle or cell wall particle, can reduce the rate of release and/or degradation of the active agent, thus increasing the duration of action of the active agent.

Active agents can be taken up and stably encapsulated within the microparticles, e.g. the hollow glucan particles or hollow cell wall particles. Encapsulation of active agents into such particles can be achieved by incubation of the particles with the active agent.

The compositions according to the present invention can provide, without limitation, the following advantages:
- maximise active agent encapsulation;
  - minimise unencapsulated active agent;
  - control active agent stability;
  - control active agent release kinetics;
  - creation of a solid form of a liquid active agent to increase the mass and uniformity;
  - simplify handling and application of the active agent;
  - mask the smell and taste of the active agent; and
  - inhibit spoilage or decomposition of the composition due to the growth of undesirable mould, yeast, and/or fungus.

The active agent component of the present invention can comprise a single active agent or a mixture of active agents.

The microparticles, active agents, terpene preservative components, surfactants, and other components of the compositions of the invention may be readily purchased or synthesised using techniques generally known to synthetic chemists.

It is highly preferred that terpenes used in the present invention, for safety and regulatory reasons, are at least food grade terpenes (as defined by the United States FDA or equivalent national regulatory body outside the USA).

The composition of the present invention can be in the form of a dry powder. The composition can be provided in combination with an acceptable carrier or excipient in a liquid, solid or gel-like form.

For solid compositions, suitable carriers include, but shall not be limited to, mannitol, lactose, starch, magnesium stearate, sodium saccharin, talc, cellulose, glucose, sucrose, magnesium carbonate, and the like.

The composition can also contain a dispersal agent which promotes dispersal of the composition when placed into a liquid, e.g. water. Suitable dispersal agents include xanthan gum, maltodextrin, alginates, or the like.

Liquid compositions can, for example, be prepared by dispersing the composition in water, saline, aqueous dextrose, glycerol, ethanol, or the like, to form a solution or suspension. If desired, these compositions can contain minor amounts of auxiliary substances such as wetting or emulsifying agents, pH buffering agents (for example, sodium acetate, sorbitan monolaurate, triethanolamine sodium acetate or triethanolamine oleate). The methods of preparing such liquid compositions are known, or will be apparent, to those skilled in this art. A liquid composition could be prepared by dispersing the composition in a pharmaceutically acceptable or an agriculturally acceptable excipient.

The composition of the invention may contain binders and lubricants. Fine powders or granules may contain diluting, dispersing and/or surface active agents and can be presented in water or in a syrup.

The composition can conveniently be in a dry state. Non-aqueous solutions or suspensions of the composition are also suitable and may contain suspending agents. Where desirable or necessary, preserving, suspending, thickening, or emulsifying agents can be included.

The composition may also contain buffers, diluents and other suitable additives.

Examples of non-aqueous solvents are propylene glycol, polyethylene glycol, vegetable oils (such as olive oil), and injectable organic esters (such as ethyl oleate). Aqueous carriers include water, alcoholic/aqueous solutions, emulsions, or suspensions, including saline and buffered media. Other vehicles include sodium chloride solution, Ringer's dextrose, dextrose and sodium chloride, lactated Ringer's, or fixed oils.

Preservatives and other additives can also be present such as, for example, antimicrobials, anti-oxidants, chelating agents, and the like.

Conventional carriers, aqueous, powder or oily bases, thickeners, and the like can be used as necessary or desirable.

The present invention also provides a method of making a microparticle delivery system as hereinbefore described, said method comprising the steps of:
- providing a microparticle, such as an extracted yeast cell wall comprising beta-glucan, the yeast cell wall defining an internal space;
- contacting the microparticle with a preservative amount of a terpene component wherein the terpene component becomes associated with microparticle; and
- contacting the microparticle with an active agent wherein the active agent becomes associated with microparticle.

It will be understood by the person skilled in the art that in the method of this aspect of the invention the terpene preservative component may be associated with the microparticle before or after the association of the active agent with the microparticle.

Alternatively, the method may comprise associating the active agent and the terpene component with the microparticle simultaneously.

The present invention further provides a method of preparing a pharmaceutical composition comprising a therapeutically effective amount of an encapsulated pharmaceutically active agent and a preservative amount of one or more terpenes, said method comprising mixing a microcapsule component with an active agent, and a preservative amount of a terpene component.

The present invention also provides a method of preparing a pesticidal composition comprising a pesticidally effective amount of an encapsulated pesticidally active agent and a preservative amount of one or more terpenes comprises mixing a microcapsule component with an active agent, and a preservative amount of a terpene component.

More specifically, the method of this aspect of the invention comprises preparing a composition comprising an active agent and a preservative amount of a terpene component wherein at least the active agent is in encapsulated form which comprises preparing a microparticle, e.g. a hollow glucan particle or hollow cell wall particle, encapsulating an active agent, said method comprising the steps of;
  a) providing a terpene component;
  b) providing a microparticle, e.g. a hollow glucan particle or cell wall particle;
  c) incubating the terpene component with the microparticle under suitable conditions, e.g. for terpene encapsulation;
  d) optionally recovering the microparticle/terpene component;
  e) providing an active agent component; incubating the active agent with the microparticle under suitable conditions, e.g. for active agent encapsulation; and
  g) recovering the microparticle/terpene component.

It will be understood by the person skilled in the art that the active agent may be encapsulated simultaneously with the terpene component. Alternatively, the active agent may be encapsulated prior to treating with the terpene component. In the preferred embodiment the microcapsule is treated with a preservative amount of a terpene component prior to the microcapsule being treated with the active agent.

Optionally the above method can further comprise the step of drying the particles encapsulating the active agent component. Drying may be achieved in a number of ways and mention may be made of freeze drying, fluidised bed drying, drum drying or spray drying, all of which are well known processes.

In step a) of the above method, the terpene component is suitably provided as a suspension in an aqueous solvent, and optionally in the presence of a surfactant. Suitably the solvent is water. A suitable surfactant is Tween-80 (polyoxyethylenesorbitan monooleate), and preferably the surfactant is present at a concentration of about 0.1 to 10% by volume of the total reaction mixture, more preferably about 1%. Alternatively the terpene component may be provided as a true solution in a solvent, e. g. water. A true solution of terpene in water can be obtained by mixing the terpene in water at high shear until a true solution is obtained.

Publication No WO 03/020024 provides further details of forming true solutions of terpenes in water.

In step b) of the above method, the microparticle, e.g. the hollow glucan particle or cell wall particle, is suitably provided as a suspension in water or other suitable liquid.

Suitably the suspension comprises approximately 1 to 1000 mg particles per ml, preferably 200 to 400 mg/ml. Alternatively the particles may be provided as a dry powder and added to the terpene-surfactant suspension.

Alternatively the particles are provided in sufficient liquid to minimally hydrate the particles, but not in significant excess. The term "hydrodynamic volume" (HV) is used to describe the volume of liquid required to minimally hydrate the particles. Thus suitably the particles are provided with a volume ranging from the HV and a volume of 1.5 times the HV (1.5HV). This makes the subsequent drying step more efficient. Also, where a low volume of liquid is used (i.e. around HV to 1.5HV), it is also possible to extrude the finished product into pellet or noodle form, which is convenient for fluidised bed drying.

It has been found that the terpene component can become encapsulated by the hollow glucan particle or cell wall particle at room temperature. The rate of encapsulation is, however, increased at 37 C but the temperature should be kept below the boiling point or denaturing temperature of any component of the composition. Suitable conditions for step c) of the above method are therefore atmospheric pressure at a temperature of 20 to 37 C. Optimisation of the conditions for a particular encapsulation reaction will be a matter of routine experimentation.

Optionally the above method can further comprise the step of drying the particles encapsulating the terpene component. Drying may be achieved in a number of ways and mention may be made of freeze drying, fluidised bed drying, drum drying or spray drying, all of which are well known processes.

The active agent component may generally be treated in a similar manner to the terpene component.

Whilst it is an object of the present invention to provide a composition comprising a microparticle component; an encapsulated active agent; and a preservative amount of one or more terpenes, it will be understood that microparticles provided with a preservative amount of one or more terpenes, i.e. prior to providing an active agent, are novel per se.

Therefore, according to a further aspect of the invention there is provided a composition comprising a microparticle and a preservative amount of one or more terpenes. Such a composition is useful, inter alia, for treatment with an active agent to form a composition of the first aspect of the present invention.

As hereinbefore described, incorporation of an active agent component in a microparticle, e.g. a hollow glucan particle or cell wall particle, can reduce the rate of release and/or degradation of the active agent, thus increasing the duration of action of the active agent.

The use of a terpene component as a microcapsule preservative is novel per se.

Therefore, according to a yet further aspect of the present invention there is provided the use of a terpene component in inhibiting or preventing the growth of undesirable moulds, yeasts, and/or fungi in microparticles.

According to this aspect of the invention the microparticles are preferably glucan particles or yeast particles, e.g. hollow glucan particles or hollow yeast particles as hereinbefore described.

According to this aspect of the invention the terpene component which may be considered to be a preservative amount or an anti-mycotic amount is ≤1% w/w, or ≤1% w/w, ≤0.9% w/w, ≤0.8% w/w, ≤0.7% w/w, ≤0.6% w/w, ≤0.5% w/w, ≤0.4% w/w, ≤0.3% w/w, ≤0.2% w/w, ≤0.1% w/w, ≤0.09% w/w, ≤0.08% w/w, ≤0.07% w/w, ≤0.06% w/w, ≤0.05% w/w, ≤0.04% w/w, ≤0.03% w/w, ≤0.02% w/w, ≤0.01% w/w of the composition.

The preservative amount or anti-mycotic amount of the one or more terpenes may be from about 0.01% w/w to about 0.99% w/w.

According to a yet further aspect of the invention there is provided a method of inhibiting or preventing the growth of undesirable moulds, yeasts, and/or fungi in microparticles, such as, glucan particles or yeast particles, e.g. hollow glucan particles or hollow yeast particles as hereinbefore described, which comprises treating the microparticles with a preservative amount or an anti-mycotic amount of a terpene component as hereinbefore described.

The invention further provides the use of a terpene in the manufacture of a preserved microparticle composition. According to this aspect of the invention the microparticle composition preferably comprises glucan particles or yeast particles, e.g. hollow glucan particles or hollow yeast particles as hereinbefore described.

Thus, the compositions of the present invention may be advantageous in that, inter alia, a variety of active agents may be encapsulated in preserved microcapsules.

The invention will now be described by way of example only.

EXAMPLE 1

6×yeast suspension samples were prepared to the following compositions:
1. Standard composition Yeast Glucan Particles (no terpenes added).
2. Standard composition plus 1 g/l geraniol.
3. Standard composition plus 1 g/l eugenol.
4. Standard composition plus 1 g/l carvone.
5. Standard composition plus 1 g/l citral.
6. Standard composition plus 1 g/l thymol.

A sample of each preparation was stored at 20° C. and 35° C. Each was checked on a weekly basis for any physical changes such as evidence of mould growth.

Tests were terminated if the assessment indicated signs of mould growth. The results are summarised in Table I:

TABLE I

| Sample ref. | Terpene added at 1 g/L | Storage temperature | Time point mould appeared | Any pressure in storage container |
| --- | --- | --- | --- | --- |
| 1 | none | 35° C. | No mould after 12 weeks | None |
|   |      | 20° C. | 4 weeks | None |
| 2 | Geraniol | 35° C. | No mould after 12 weeks | None |
|   |          | 20° C. | No mould after 12 weeks | None |
| 3 | Eugenol | 35° C. | No mould after 12 weeks | None |
|   |         | 20° C. | No mould after 12 weeks | None |
| 4 | Carvone | 35° C. | No mould after 12 weeks | None |
|   |         | 20° C. | No mould after 12 weeks | None |
| 5 | Citral | 35° C. | No mould after 12 weeks | None |
|   |        | 20° C. | No mould after 12 weeks | None |
| 6 | Thymol | 35° C. | No mould after 12 weeks | None |
|   |        | 20° C. | No mould after 12 weeks | None |

The only sample where any mould growth was observed was in the control sample No. 1 (no terpene added) stored at 20° C.

The invention claimed is:

1. A composition comprising a microparticle component comprising hollow yeast cell wall particles or hollow glucan particles; an encapsulated active agent; wherein the microparticle component encapsulates one or more terpenes, and wherein the one or more terpenes is present in a preservative amount of less than or equal to 0.7% w/w of the microparticle component.

2. A composition according to claim 1 wherein the composition further includes an active agent encapsulated in the microparticle component.

3. A composition according to claim 1 wherein the terpene is geraniol, eugenol, carvone, citral, or thymol.

4. A composition according to claim 1 wherein the one or more terpenes comprises geraniol.

5. A composition according to claim 1 wherein the one or more terpenes comprises eugenol.

6. A composition according to claim 1 wherein the one or more terpenes comprises carvone.

7. A composition according to claim 1 wherein the one or more terpenes comprises citral.

8. A composition according to claim 1 wherein the one or more terpenes comprises thymol.

9. A composition according to claim 1 wherein the hollow glucanparticle or cell wall particle has a lipid content of >1% w/w.

10. A composition according to claim 2 wherein the active agent is a biologically active agent.

11. A composition according to claim 10 wherein the biologically active agent is a pesticide, plant nutritive substance or plant growth regulant.

12. A composition according claim 2 wherein the composition comprises from about 1% w/w to about 90% w/w, of the active agent component based on the total composition.

13. A microparticle delivery system comprising a microparticle, an encapsulated active agent and a preservative amount of a terpene component, wherein the microparticle component comprises hollow yeast cell wall particles or hollow glucan particles, and wherein the microparticle component encapsulates one or more terpenes, and wherein the one or more terpenes is present in a preservative amount of less than or equal to 0.7% w/w of the microparticle.

14. A method of delivering an active agent to a recipient, comprising administering to a recipient the composition of claim 1.

15. A method according to claim 14 wherein the recipient is an arthropod.

16. A method of killing a pest, comprising administering an affective amount of the composition of claim 1 to a pest.

17. A method of killing a pest according to claim 16 wherein the pest is an arthropod.

18. A method of killing a pest according to claim 16 wherein the pest is a fungus.

19. A method of killing a pest according to claim 16 wherein the pest is a bacteria.

20. A method of inhibiting or controlling the growth of undesirable moulds, yeasts, and/or fungi in microparticles, comprising encapsulating within the microparticles an active agent and a preservative amount of less than or equal to 0.7% w/w of a terpene component, wherein the microparticles comprise hollow glucan particles or hollow yeast particles.

* * * * *